United States Patent
Katsuta et al.

(10) Patent No.: US 7,272,253 B2
(45) Date of Patent: Sep. 18, 2007

(54) METHOD FOR NON-DESTRUCTIVE INSPECTION, APPARATUS THEREOF AND DIGITAL CAMERA SYSTEM

(75) Inventors: Daisuke Katsuta, Yokohama (JP); Mineo Nomoto, Yokohama (JP); Tetsuo Taguchi, Hitachi (JP); Masahiro Hotta, Hitachi (JP); Isao Tanaka, Tokai (JP)

(73) Assignee: Hitachi, Ltd., Tokyo (JP)

( * ) Notice: Subject to any disclaimer, the term of this patent is extended or adjusted under 35 U.S.C. 154(b) by 420 days.

(21) Appl. No.: 10/057,562

(22) Filed: Jan. 25, 2002

(65) Prior Publication Data

US 2002/0154811 A1    Oct. 24, 2002

(30) Foreign Application Priority Data

Feb. 9, 2001  (JP)  ............... 2001-033087

(51) Int. Cl.
*G06K 9/00* (2006.01)
*G06K 9/36* (2006.01)
*G06K 9/32* (2006.01)
*H04N 7/18* (2006.01)
*H04N 9/47* (2006.01)

(52) U.S. Cl. .............. 382/141; 382/108; 382/154; 382/284; 382/287; 382/294; 348/125

(58) Field of Classification Search ........... 382/108, 382/141–143, 145, 148–149, 151, 154, 284–287, 382/294–297; 345/125–134
See application file for complete search history.

(56) References Cited

U.S. PATENT DOCUMENTS

| | | | | |
|---|---|---|---|---|
| 5,140,647 A | * | 8/1992 | Ise et al. | 382/284 |
| 5,257,325 A | * | 10/1993 | Casparian et al. | 382/294 |
| 5,469,274 A | * | 11/1995 | Iwasaki et al. | 358/450 |
| 5,621,817 A | * | 4/1997 | Bozinovic et al. | 382/189 |

(Continued)

FOREIGN PATENT DOCUMENTS

EP    1167964 A1    1/2002

(Continued)

*Primary Examiner*—Bhavesh M Mehta
*Assistant Examiner*—Manav Seth
(74) *Attorney, Agent, or Firm*—Townsend and Townsend and Crew LLP

(57) ABSTRACT

An image input can be executed without any influence of physical conditions of an inspection object and environment such as installation area by utilizing a cordless type image pickup apparatus in the excellent portability combining a lighting apparatus to a digital camera. On the occasion of picking up an image of such inspection object, marks of the shape such as the rectangular shape, circular shape and linear line shape and marks of the shape combining the linear lines (plus sign (+), capital letter L or cross (+)) of known size are allocated within the same image and these marks are extracted simultaneously. Thereby, compensation process for the magnifying factor, position and tilt is conducted using the marks allocated in the image with the equal interval. Input data is continuously applied depending on the inspection object to generate a total inspection map by combining such input data. A computer executes a flaw detection process and stores the processing result in the form of a file together with the inspection images. Thereby, an inspection management system for search using information and inspection result of the inspection object as the characteristics element can be established.

8 Claims, 19 Drawing Sheets

U.S. PATENT DOCUMENTS

| | | | |
|---|---|---|---|
| 5,663,806 A * | 9/1997 | Grise et al. | 382/287 |
| 6,078,701 A * | 6/2000 | Hsu et al. | 382/294 |
| 6,424,752 B1 * | 7/2002 | Katayama et al. | 382/284 |
| 6,744,931 B2 * | 6/2004 | Komiya et al. | 382/284 |
| 6,978,052 B2 * | 12/2005 | Beged-Dov et al. | 382/284 |
| 7,009,638 B2 * | 3/2006 | Gruber et al. | 382/294 |
| 2002/0126890 A1 * | 9/2002 | Katayama et al. | 382/154 |
| 2003/0076406 A1 * | 4/2003 | Peleg et al. | 348/36 |

FOREIGN PATENT DOCUMENTS

| | | |
|---|---|---|
| JP | 06-118062 | 4/1994 |
| WO | WO 00/60344 | * 10/2002 |

* cited by examiner (CONTINUOUS IMAGE)

(CONTINUOUS IMAGE)

IMAGE OF CHROMATICITY

IMAGE OF HUE

IMAGE OF CHROMATICITY

IMAGE OF COLOR DIFFERENCE

DIFFERENTIAL VALUE OF COLOR DIFFERENCE

DIFFERENTIAL VALUE OF COLOR DIFFERENCE

FIG. 23A (PLACE)
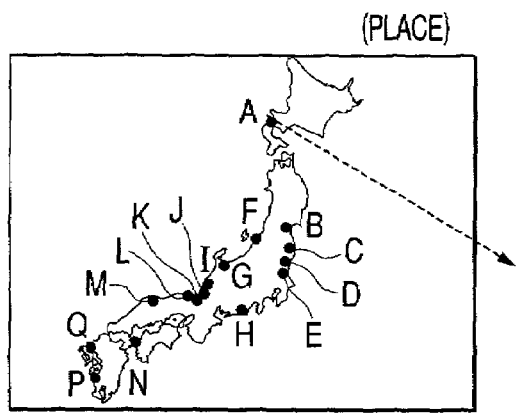
FIG. 23B (AN AREA OF FACILITY)
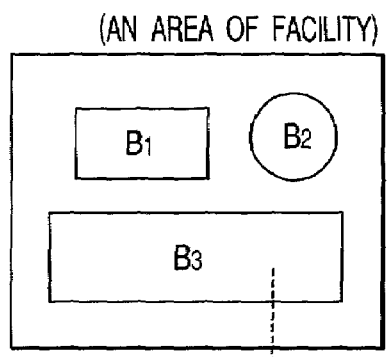
FIG. 23D (FLAW AREA)
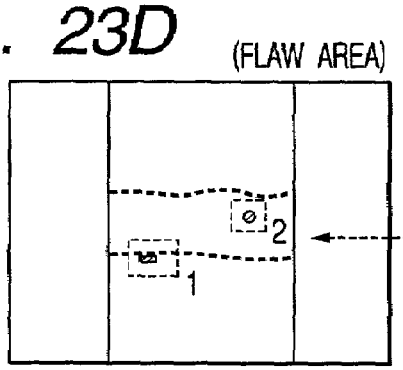
FIG. 23C (PIPING SYSTEM)
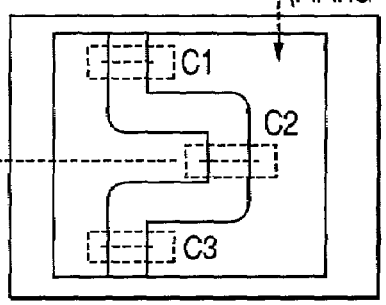
FIG. 23E
| INSPECTION DATA | PLACE | AREA OF FACILITY | PIPING SYSTEM | FLAW AREA |
|---|---|---|---|---|
| '99/3 | A | B3 | C2 | 1~2 |
| '99/9 | A | B3 | C2 | 1~2 |
| '00/3 | A | B3 | C2 | 1~2 |
| '00/9 | A | B3 | C2 | 1~2 |
FIG. 23F
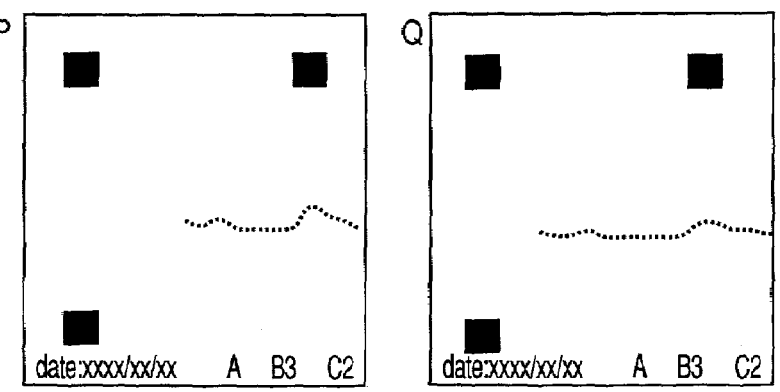

METHOD FOR NON-DESTRUCTIVE INSPECTION, APPARATUS THEREOF AND DIGITAL CAMERA SYSTEM

FIELD OF THE INVENTION

The present invention relates to a method and an apparatus for non-destructive inspection of a flaw such as a surface crack or the like of metal and ceramics and particularly to a method and an apparatus for non-destructive inspection based on the inspection method which is called as a liquid penetrant inspection and a magnetic particle inspection.

DESCRIPTION OF THE RELATED ART

The liquid penetrant inspection and magnetic particle inspection for visual inspection of flaw such as surface crack of metal and ceramics or the like are specified by JIS W 0904 and JIS Z 2343, etc. and these inspection methods require various conditions of evaluation environment by inspection personnel having the recognized skills.

Moreover, the Japanese Unexamined Patent Publication No. Hei 6-118062 discloses, as a method for liquid penetrant inspection of a vane of runner of water wheel of the known shape and size, a method for calculating the position of a flaw from the shape and size by inputting an image to a fixed camera.

The visual inspection specified by the JIS explained above has following problems:
(1) An inspection person unfortunately overlooks a fault because he is very much tired or inspection result is different dependent on personal difference of the inspection person.
(2) The inspection result is expressed in a report or the like only with the wording of "Passed" and if re-inspection is required due to generation of a problem, reliability of inspection includes a certain question because a practical change is still unknown and there is no reproducibility.
(3) When a TV camera or the like is used,
(3a) the camera can be fixed for use in such a case that an inspection object, for example, a runner of water wheel which is a part of a water wheel power generator moves but when the inspection object is a fixed one such as a plant piping, the inspection range is restricted for the inspection which is executed by drawing a longer camera cable.
(3b) When an image pickup device such as a TV camera is moved to the inspection area and an image input is conducted, there rises a problem that magnification and tilt of image are different in every image to be picked up.
(3c) Moreover, in the case of piping inspection and bridge inspection of a large-size plant, a large amount of input image is required and the inspection condition is evaluated by searching the inspection result. In this case, it can be expected that many procedures and longer time are required and thereby the evaluation work is very much complicated.

SUMMARY OF THE INVENTION

It is therefore an object of the present invention to provide a method and an apparatus for flaw inspection using an apparatus having excellent portability and a method and an apparatus for management of inspection results assuring easier data search.

In view of achieving the object explained above, the present invention can pick up an image of the inspection object using a cordless type imaging apparatus having excellent portability in which the power supply cable and signal cable or the like have been eliminated by combining a color image pickup means having excellent portability such as a digital camera or the like and a lighting apparatus.

For picking up of a plurality of areas of an inspection object and matching of magnifications, positions and tilts of images of a plurality of positions, the marks A of the shape such as rectangular shape, circular shape and linear line shape and of the shape formed by combining linear lines (plus sign (+), capital letter L or cross (+)) of known size are allocated to an image display apparatus of a color image pickup means and the marks B are also allocated on the inspection object. Here, the inspection object image is picked up under the condition that the sizes and positions of the marks A and marks B are almost matched. Moreover, magnification, position and tilt are compensated to become the constant values with an image processing means using the marks B of the image picked up, candidates of flaw are extracted from a plurality of compensated inspection object images, the images of flaw candidates extracted are displayed on the display area (screen), an image extracted from the images of flaw candidates displayed is then stored in a memory means and the stored image is displayed again on the display area.

Even in the case where the inspection result and detected image of a long-length object having the area larger than image detection range of the image pickup means are confirmed with the display apparatus, magnifications, positions and tilts of the respective detected images are compensated with the image processing means to become constant, a plurality of inspection object images are continuously joined using the marks B and the image is displayed again on the display area under the positioning condition.

Particularly, in the inspection method such as a liquid penetrant inspection method or the like to determine a flaw depending on chromaticness and luminosity of color of the penetrant in the flaw, the inspection object is lighted with color temperature within the predetermined range in the predetermined time required for picking up an image so that it has been eliminated that a defective area is detected erroneously and overlooked because of generation of changes in chromaticness and luminosity of color of penetrant penetrated into the defective area due to the change of color temperature of the lighting beam.

A kind of inspection object is sorted based on the similarity P [shape of flaw (circular shape, linear shape, area and position), color information (chromaticity, maximum chromaticity, maximum luminance, differential value), size (length, width, aspect ratio)] in regard to information of the inspection object having completed the inspection, a kind of a flaw candidate is sorted based on the similarity Q [material, YES or NO of inspection for welding, name of inspection field, name of factory, name of plant, name of building, name of piping system, piping number, diameter of piping, thickness of pipe, time of implementation-or the like] in regard to information of the flaw candidate, characteristics of inspection object and flaw candidate are extracted based on the sorted result and such extracted characteristics of inspection object and flaw candidate are fed back to display a similar flaw and similarity inspection department and to assure easier inspection and search or the like.

Moreover, the present invention also utilizes a digital camera system comprising a lens portion, a shutter portion, a light for emitting uniform light beam provided near the lens portion, a recording medium for electronically storing the images picked up, a battery and a display unit.

These and other objects, features and advantages of the invention will be apparent from the following more particular description of preferred embodiments of the invention, as illustrated in the accompanying drawings.

BRIEF DESCRIPTION OF THE DRAWINGS

FIG. 6A shows an input image, FIG. 6B shows an image after compensation for tilt and FIG. 6C shows an image after positional compensation.

FIG. 9A shows a flaw image and FIG. 9B shows development of flaw on a chromaticity diagram.

FIG. 16A is a graph showing the number of pixels in the x chromaticity and y chromaticity. FIG. 16B is a graph showing x chromaticity of the reference color. FIG. 16C is a graph showing y chromaticity of the reference color.

FIG. 17A shows a chromaticity image. FIG. 17B is a graph of x chromaticity and y chromaticity for the reference chromaticity. FIG. 17C shows a hue image.

FIG. 18A shows a chromaticity image. FIG. 18B is a graph of x chromaticity and y chromaticity for the reference chromaticity. FIG. 18C shows a color difference image.

FIG. 20A is a diagram showing the flaw candidate area. FIG. 20B is a graph showing color difference from the reference white. FIG. 20C is a diagram showing a flaw area of the clear contour. FIG. 20D is a graph showing a differential distribution of color difference.

FIGS. 23A, 23B, 23C, 23D, 23E and 23F are show an example of the data filing system, namely an image file format in which the information pieces such as name of factory, name of piping system and time of implementation are defined as similarity. FIG. 23A shows an inspection place. FIG. 23B shows an area of facility. FIG. 23C shows a piping system. FIG. 23D shows a result of the liquid penetrant inspection method. FIG. 23E shows a filing example of FIGS. 23A to 23D. FIG. 23F shows an example of monitoring display of image data.

DESCRIPTION OF THE PREFERRED EMBODIMENTS

The preferred embodiments of the present invention will be explained in detail with reference to the accompanying drawings.

Figure 1:
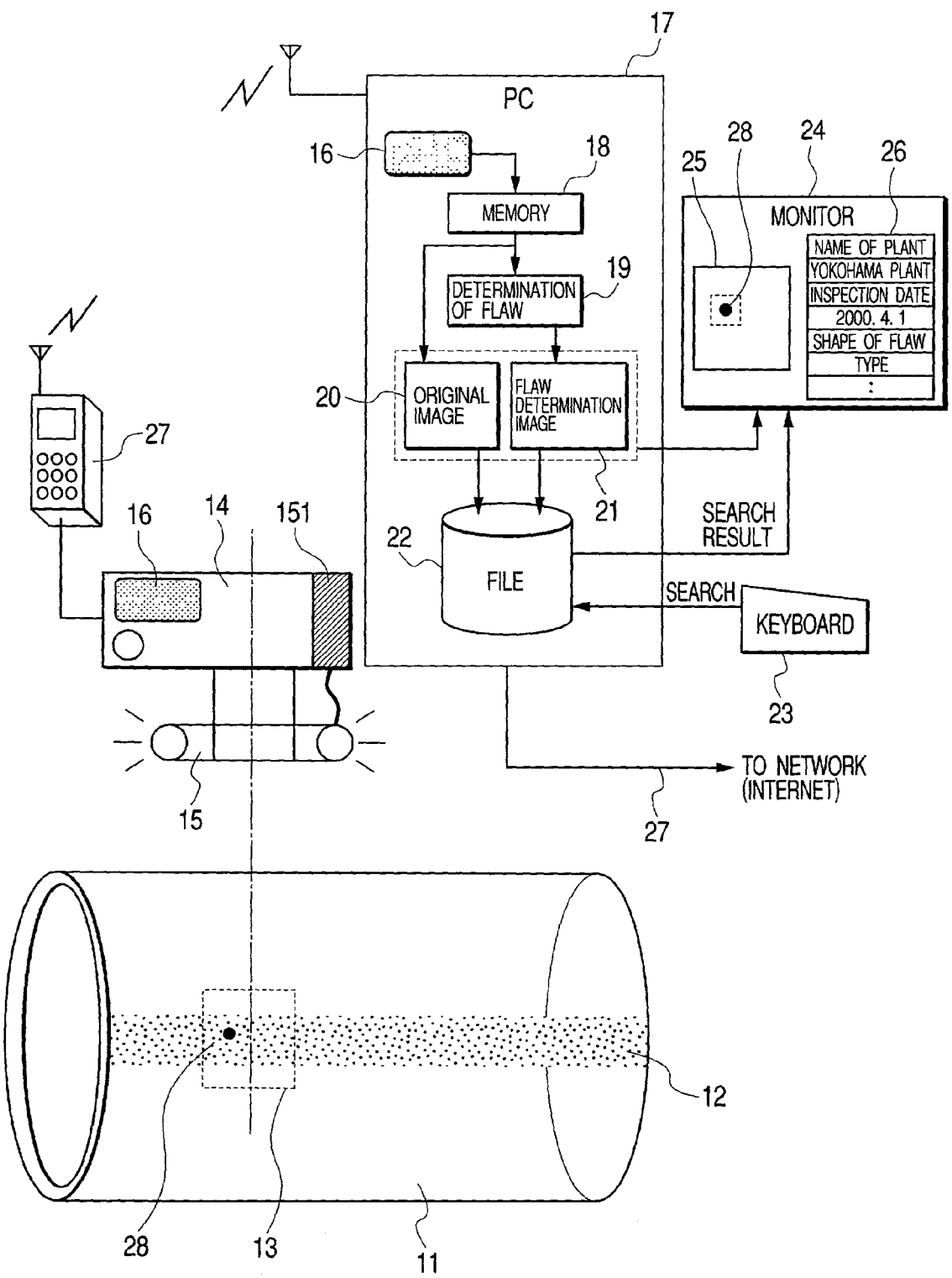
FIG. 1 is a schematic structural diagram showing an example of a penetrant inspection apparatus of the present invention for the welded portions of piping.

FIG. 1 is a schematic structural diagram showing an example of a liquid penetrant inspection apparatus of the present invention.

An inspection object 11 is a metal piping part for inspection of welded portion where welding beads 12 exist in the horizontal direction of the figure. For the liquid penetrant inspection, the surface of the metal piping part including the welding beads 12 is coated with a red-color solvent and this solvent is removed after several minutes. However, if a flaw such as crack or the like exits in the area coated with the red-color solvent, this red-color solvent penetrated into the flaw such as crack or the like cannot be removed and is left as it is. Next, the surface area of the metal piping part from which the coated red-solvent is removed is then coated with a white-color developer. In this case, if a flaw such as crack or the like exists in the area coated with the red-color solvent, the red-color solvent remaining in the flaw is spread out to the surface of developer from the flaw area due to the capillarity of coated developer to change the developer of white-color to red-color. The welded beads portion 12 which is-free from flaw remains in the white-color (color of the developer).

The inspection area 13 including the welded-beads 12 is lighted with the LED ring light 15 for picking up with a digital camera 14 and an image is then inputted. A flaw 28 can be found in the inspection area 13. This digital camera 14 includes a built-in battery 151 for ring light. The LED ring light 15 is integrated with the digital camera 14, enabling that an image can always be picked up and can be inputted under the same lighting conditions.

An image data picked up is recorded to a recording medium 16 such as a memory card or the like. This recording medium 16 can be taken out from the digital camera 14 and can then be set to a computer 17. Thereby, the recorded image data can be read and is then stored to a large size memory 18 such as a hard disk.

Moreover, images picked up with the digital camera 14 can be stored in direct to the computer 17 through the communication by connecting the digital camera 14 to a terminal (mobile telephone) for data communication 27 and then transmitting images to the digital camera 17. For example, the computer 17 is installed in the management office of a factory and an inspection person carrying the digital camera 14 goes to the inspection field (piping structure or bridge or the like) provided in isolation from the management office, picks up images of flaw candidates and then inputs the images for the purpose of image input and thereafter inputs or transfers the data to the computer 17 from the recording medium 16 or terminal 27 for data communication.

Here, an inspection system which assures excellent mobility and portability can be attained because the image process for determining a flaw can be executed with the computer 17 and the digital camera 14 can be isolated from the computer 17 by using the recording medium 16 and data communication terminal 27 or the like for the input.

The computer 17 executes image process (explained later) to the images recorded in the memory 18 for the purpose of flaw determination 19. A flaw extracted with this process is reflected on an original image 20 to generate a flaw determination image 21. An image 25 can be checked with a color monitor 24. Information pieces such as shape, color and size of the flaw detected with the flaw determination process 19 are filed in a file 22 together with the original image 20 and flaw determination image 21. Moreover, each item of flaw information 26 is displayed on the color monitor 24 together with the image 25. Moreover, when a search instruction, for example, Yokohama plant and inspection date and time are inputted from an external keyboard 23 using the flaw information as the keyword, the related information pieces can be picked up and the information 26 and image 25 can be displayed on the color monitor 24 as the search result. Therefore, change by aging from the last year, for example, can be monitored by observing the display on the color monitor 24.

The computer 17 is connected to a network with a communication cable 27 and it is possible to search the information of file 22 of this computer 17 from the other computers.

The digital camera 14 used in this embodiment shown in FIG. 1 is provided with the basic functions such as, (1) an image pickup element is a two-dimensional CCD which can detect at a time the two-dimensional area;
(2) an image pickup lens is a single focal point lens or a zoom lens forming an image focusing optical system;
(3) automatic focusing function is provided;
(4) the white balance function is provided;
(5) the monitor function to observe the image pickup condition is provided;
(6) the strobe function is also provided;
(7) the power supply is formed of a battery (alkali battery) or a chargeable battery;
(8) a recording medium is formed of a card type recording medium and the recorded image data can be inputted to a computer using a floppy disk drive or the like; and
(9) the recording system is of an image file format such as JPEG and TIFF or the like; and can be used as the image pickup means in this embodiment.

The digital camera 14 is usually provided with a strobe for picking up images in the dark environment by emitting the strobe light. However, in general, white balance (a function to pick up a white area as a white image in accordance with a light source (color temperature) in the imaging condition) is in some cases automatically set in the condition of picking up an image through the emission of strobe light and since dependent compensation is automatically added by estimating the condition of light source from the image pickup condition, the color of the image picked up is likely different from the actual color of the object.

Therefore, when an image can be picked up with a digital camera having the function to manually set the white balance, since a color temperature of the light source which can be calculated inversely from a result of previous imaging of a white object as the reference of the imaging object can be reflected on the color compensation for the images to be picked up subsequently, the color of image picked up can reproduce the color of the imaging object.

Figure 2:
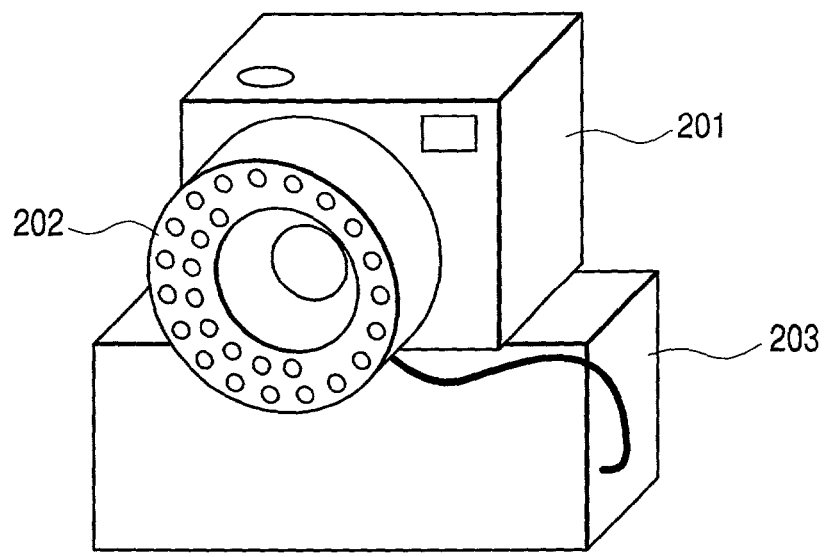
FIG. 2 is a perspective view of a cordless type image input apparatus in which an LED ring lighting device is mounted to a digital camera of the present invention.

FIG. 2 shows a digital camera system 200 which can realize high precision regeneration of color by the present invention. This digital camera system 200 mounts the LED ring light 202 as the light source of the lighting to a digital camera body 201 and sets the white balance corresponding to the color temperature of light source in order to detect an image. The LED ring light 202 mounted at the external circumference of the camera body 201 is provided with a diffusion plate (not shown) to uniformly irradiate the imaging object with the lighting beam and to provide uniform distribution of illuminance.

As the power supply of the LED ring light 202, a battery 203 using a battery (alkali battery or the like) or a chargeable battery or the like is utilized like the power supply of the digital camera body 201 and this battery 203 also has the function to control the power feeding to the ON/OFF conditions.

The digital camera system 200 shown in FIG. 2 integrates the digital camera body 201, LED ring light 202 and battery 203 to provide the structure to be held and carried very easily. In the case of the digital camera system 200 in the structure shown in FIG. 2 manufactured in trial, eight (8) type-1 nickel cadmium storage batteries are used as the battery for charging the battery 200, but in this case, it has been confirmed that the digital camera system 200 can be formed in the weight of 5 kg or less and also can be easily held and carried. In the digital camera system 200 shown in FIG. 2, the LED ring light 202 is used as the light source for the lighting system, but the similar effect can also be obtained by using, in addition, a fluorescent bulb, incandescent lamp, halogen fiber light source, cathode bulb or the like as the light source.

Figure 3:
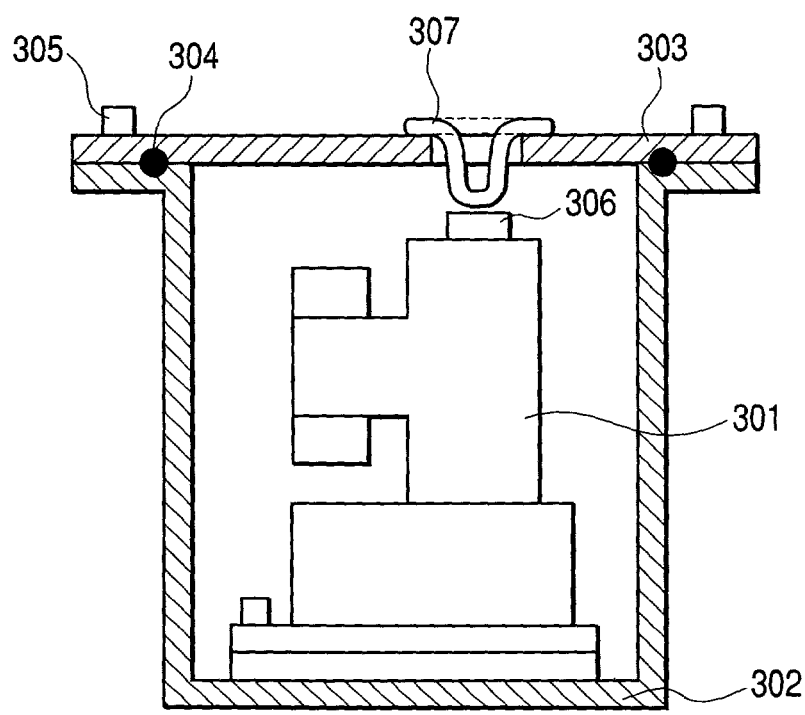
FIG. 3 shows a profile of the image input apparatus of FIG. 2 which is provided with a waterproof and dust-proof cover.

FIG. 3 shows a profile of the image input apparatus which is accommodated for the imaging within a waterproof and dust-proof cover. In the case of picking up an image using the strobe function of the digital camera or using an image pickup apparatus of the embodiment shown in FIG. 2, the image pickup apparatus body 301 is covered with a water-proof and dust-proof cover consisting of the front cover 302 and rear cover 303 for the imaging operation. Thereby, the imaging operation can be realized very easily even under the rainy, snowy or humid and dusty environment.

In the embodiment shown in FIG. 3, the water-proof and dust-proof cover is formed of a transparent resin material and the aligning portion-of the front cover 302 and rear cover 303 is sealed with an O-ring 304 and is also fixed with screws 305. A cover provided near a shutter portion 306 of camera is formed of a soft material member 307 and thereby the shutter and the power switch can be manipulated very easily. As shown in the embodiment of FIG. 3, since the function, to pick up an image through accommodation within the waterproof and dust-proof cover is provided, flaw inspection can be realized not depending on the weather condition.

Figure 4:
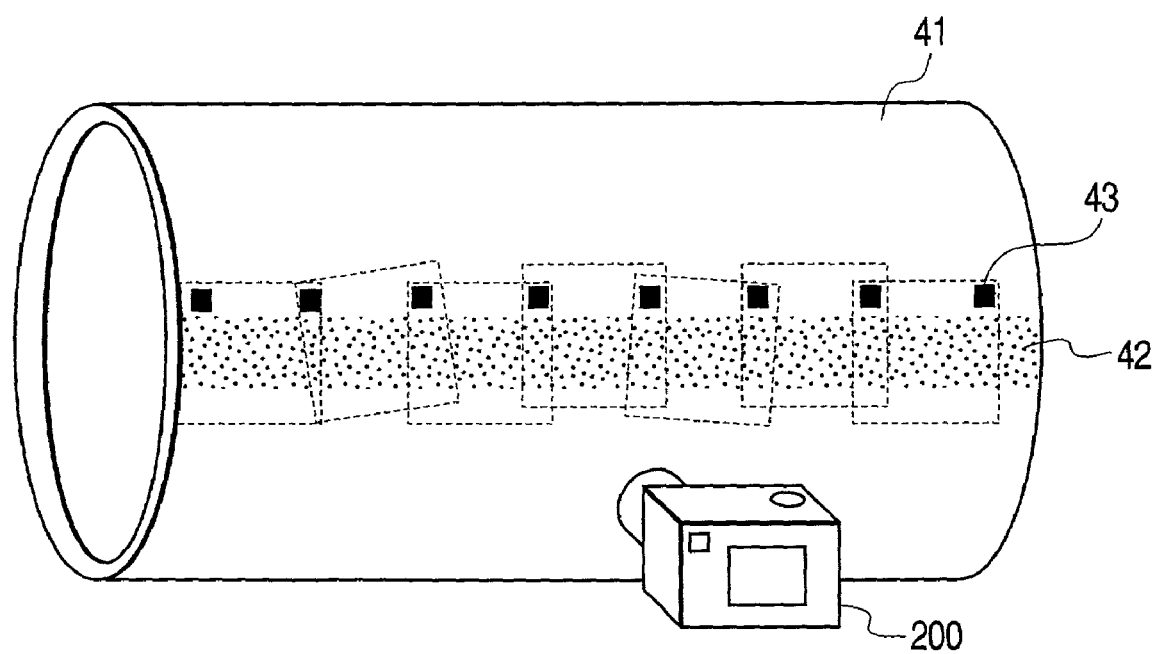
FIG. 4 is a model diagram showing an embodiment of an input image used in the liquid penetrant inspection for the piping using the image input apparatus of FIG. 2.

FIG. 4 shows an example of flaw inspection for a piping member. In this example, the welded beads 42 exist in the horizontal direction of the pipe 41 and seven (7) images are aligned for the flaw inspection of a single pipe. Regarding the procedures for flaw inspection, total area of the welded beads 42 in the horizontal direction is imaged as the first step as shown in FIG. 4. When a long-length imaging object like a pipe member shown in FIG. 4 is used, it is difficult, in some cases, to bring the total area of inspection object of the pipe member into only one viewing field of the camera because of the relationship between the resolution of camera and the minimum size of flaw to be detected. Therefore, in the case shown in FIG. 4, the total area of welded beads 42 is imaged by picking up for seven times the images through a little overlap between respective images in order to prevent generation of the non-pickup area while the imaging area is sequentially moved by setting, for example, the window 43 as the range of viewing field of camera.

As shown in FIG. 4, on the occasion of inspecting a long-length imaging object such as a pipe member 41 by dividing the imaging area thereof and then aligning the images obtained by sequentially imaging the divided areas thereof using the digital camera system 200 shown in FIG. 2, the focused pickup images can be obtained with the automatic focusing function of the digital camera body 201. However, since the digital camera system 200 of the present invention is structured to be held by hands of an inspection person and to pick up an imaging object on the non-contact basis, it is difficult to pick up images of the divided areas under the same condition on the occasion of sequentially picking up the images of divided areas and magnification factor, rotation and tilt among respective images are little different in the images obtained actually.

Figure 5:
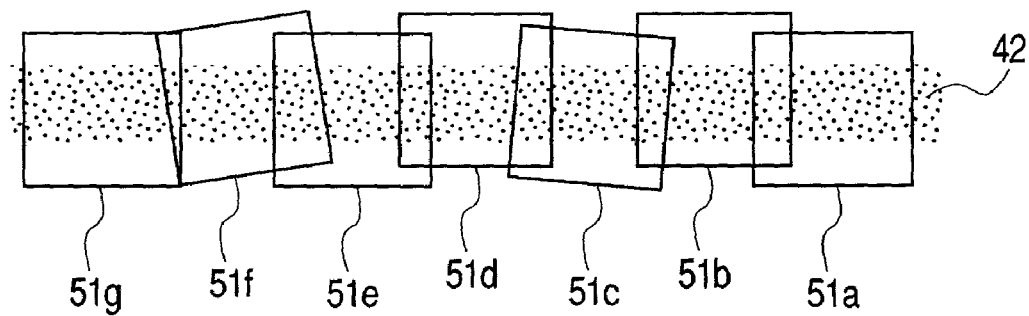
FIG. 5 is a schematic diagram in which seven images inputted in FIG. 4 are aligned to re-form the inspection surface of piping as the single sheet of image.

An image obtained by picking up the inspection object shown in FIG. 4 using the digital camera 200 is shown in FIG. 5. In this figure, the images 51a to 51g obtained by imaging operation using the digital camera system 200 are rotated, deviated in position in the vertical direction or deviated in the magnification factor for the horizontal direction of welding of the welded beads 42. Therefore, the relative positions are deviated in some cases among the images even of the same flaw and thereby a certain compensation for rotation, horizontal and vertical directions and magnification is necessary. Accordingly, as the next step of the imaging operation, compensation for rotation, horizontal and vertical directions and magnification factor of each image is executed for a plurality of images obtained through the imaging operation.

Figure 6A:
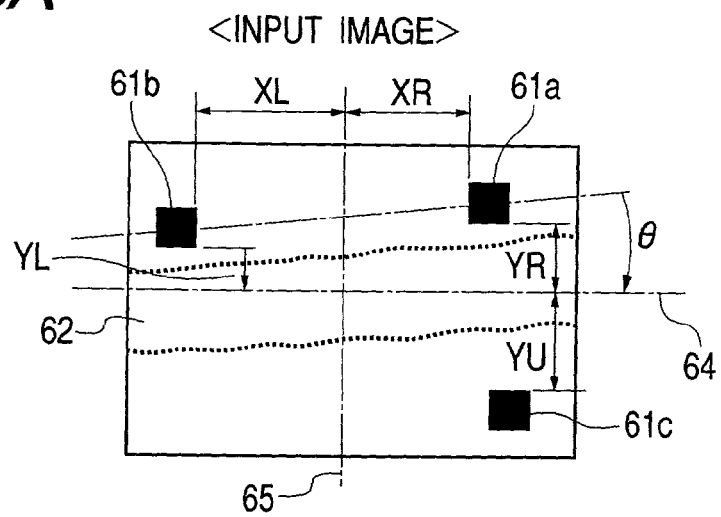
FIGS. 6A, 6B and 6C are image processing diagrams showing the method for compensation of input image, tilt and positional deviation in the present invention.

Such compensation processing procedures will then be explained with reference to FIG. 6. FIG. 6A shows an input image which is picked up in such a manner that the positioning marks 61a, 61b, 61c are given to the inspection object and these three marks are brought into only one viewing field. When the horizontal and vertical lines passing the center of CCD are defined as the horizontal reference line 64 and the vertical reference line 65, positional deviation in the vertical direction of FIG. 6A can be determined from the distances YR, YU between the horizontal reference line 64 and marks 61a, 61b, while positional deviation in the horizontal direction can also be determined from the distances XR, XL between the vertical reference line 65 and marks 61a, 61b and angular deviation of rotating angle θ can also be determined from YL, YR in FIG. 6A and therefore the positioning can be completed by executing compensation to provide the relationships of YR=YU, XR=XL and YR=YL.

Figure 6B:
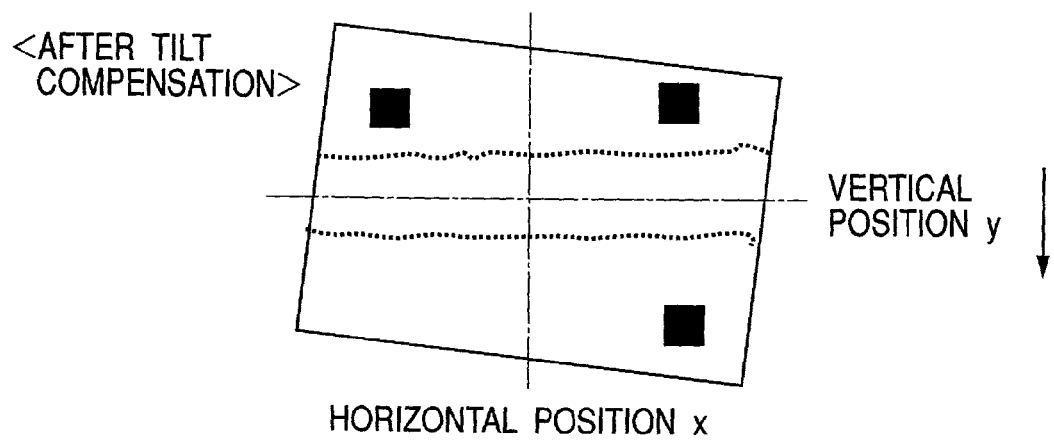
Figure 6C:
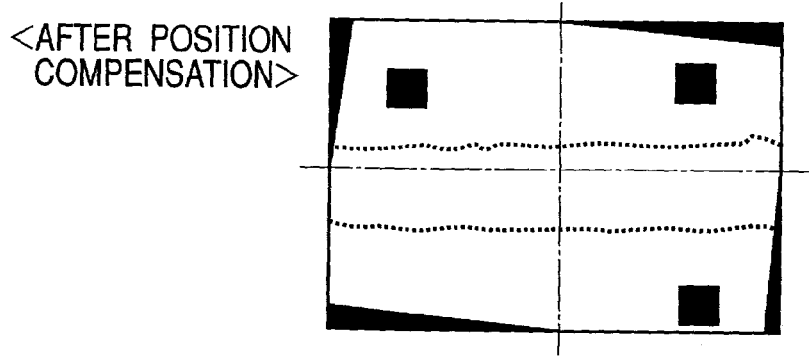

Here, this position is then relocated to the position tilted for the angle θ from the marks 61a, 61b with definition of the reference intersecting point as the neutral point. FIG. 6B shows the figure after the tilt compensation through the conversion of the angle θ for the pixels. Next, FIG. 6C shows the profile of compensation to obtain the result of YR=YU, XR=XL.

The absolute position of the flaw candidate can be detected by executing the positional compensation to seven (7) images of FIG. 4 in which this process is previously inputted.

Figure 7:
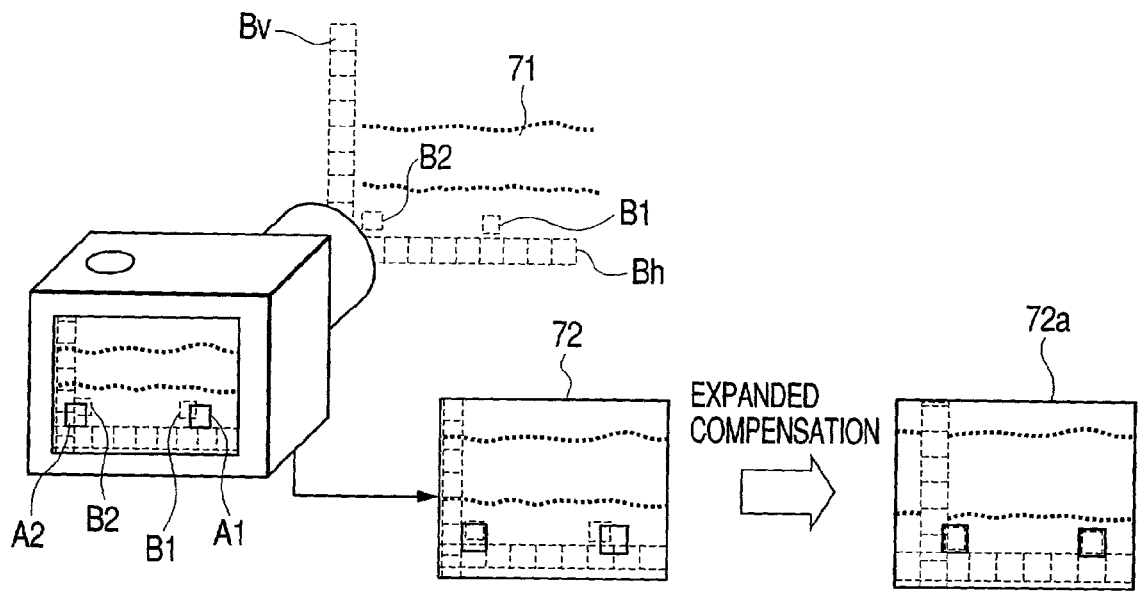
FIG. 7 shows a compensation process image after execution of the magnification factor compensation process by simultaneously imaging the marks allocated in the equal interval of the present invention.

For further high precision positional compensation, compensation for magnification factor is also conducted. FIG. 7 shows an embodiment of this compensation. Near the welded beads 71 of the inspection object, the marks B1, B2 and the lines Bh, By allocated in the equal interval are provided. On the other hand, a monitor 72 is connected to the digital camera system 200 and this monitor 72 is also given the marks A1, A2. An interval between the marks A1 and A2 is set at the position to become equal to the interval between the marks B1 and B2 on the input image. On the monitor 72, the position of the digital camera system 200 is adjusted to almost obtain the matching between the marks A1 and B1 and between the marks A2 and B2 and thereafter the inspection object images are picked up as the input images. These input images sometimes include a little deviation of magnification factor resulting from camera-shake and therefore a monitor image 72 can be attained by conducting the expansion and compression processes to provide the best matching between the mark A1 and mark B1 and between the mark A2 and mark B2 on the monitor 72.

These expansion and compression processes can easily be realized with the methods described, for example, in the Paragraph 4.1.4 Geometrical Compensation of the reference "Image Engineering" (written by Toshi Minami, Nou Nakamura, published by Corona Publishing Co., Ltd.) or in the Paragraph 3.3 Calculation for Expansion, Compression and Rotation of the reference "Industrial Image Processing" (written by Masakazu Ejiri, published by Shokodo Publishing Co., Ltd.).

With an image input during the positioning, tilt compensation and magnifying factor compensation using the marks A1, A2, marks B1, B2, Bh, Bv as explained above and moreover accuracy compensation through image process using these marks, highly accurate positioning, tilt compensation and magnifying factor compensation for a plurality of images can be realized, assuring the effect that a minute flaw or a flaw generated at the aligning area of images can also be inspected without any overlooking. In this embodiment, the magnifying factor compensation is conducted after the positioning, but it is obvious that detail position compensation can be implemented after alignment of the magnifying factor.

Figure 8:
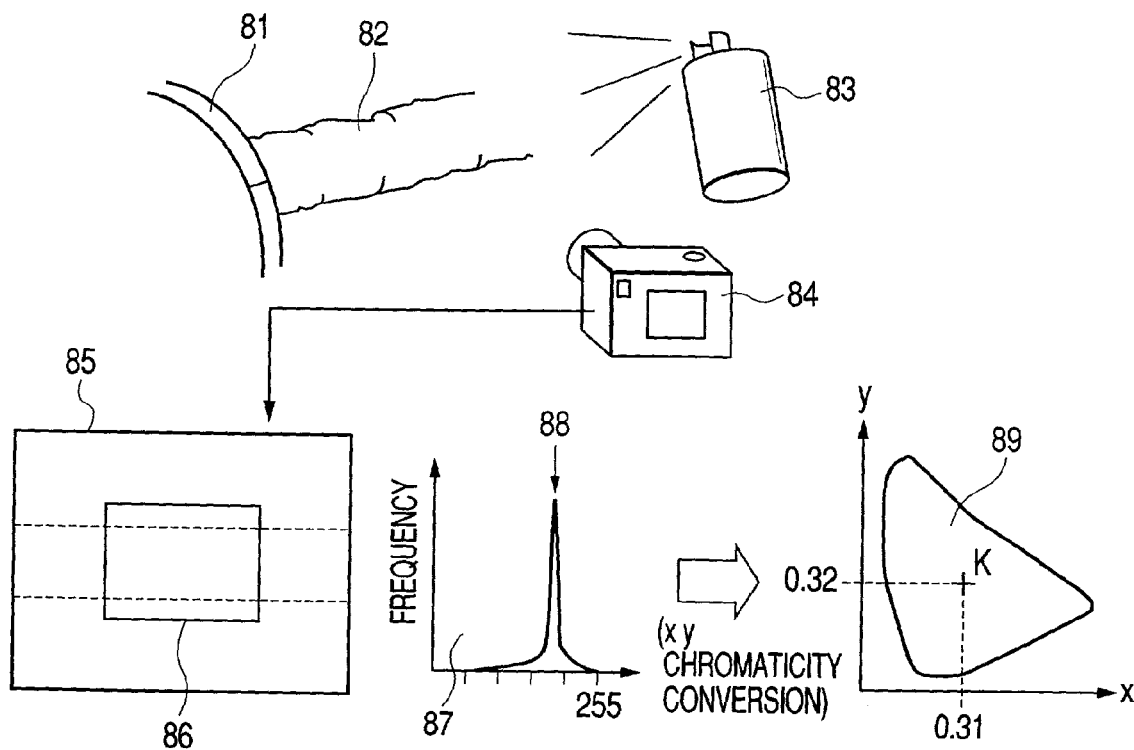
FIG. 8 shows an algorithm for determining the chromaticity of reference white from an input image of inspection object coated with a developer of the present invention.

Therefore, a flaw can be detected with the method shown in FIG. 8 and FIG. 9 using the images to which various compensations are executed. However, prior to implementation of this flaw detection, the procedures to generate continuous image by aligning a plurality of these images after the compensation processes of magnifying factor, tilt and position of each image among a plurality of images explained above are conducted will be explained with reference to FIGS. 10A to 10C and FIGS. 11A to 11C. FIG. 10A to FIG. 10C respectively show the procedures to form a continuous image when the welding is performed in the longitudinal direction of the pipe, while FIG. 11A to FIG. 11C respectively show the procedures to form a continuous image when the welding is performed in the circumferential direction.

The welding of the pipe 101 of FIG. 10A is performed in the vertical direction and the marks 106, 107, 108, 110 are allocated in the equal interval along the welded beads 109. When the range of imaging operation of an image pickup apparatus is defined to 30 MM, the input images are defined as 103, 104 and 105 in FIG. 10B. Since these images respectively include tilt and positional deviation, the compensation for magnifying factor, tilt and position is conducted respectively for the images with the method explained with reference to FIG. 6. A continuous image has been obtained by aligning above images 103, 104 and 105 as shown in FIG. 10C with reference to the marks allocated in the equal interval. Thereby, a flaw map of the pipe 101 can be generated.

Figure 10A:
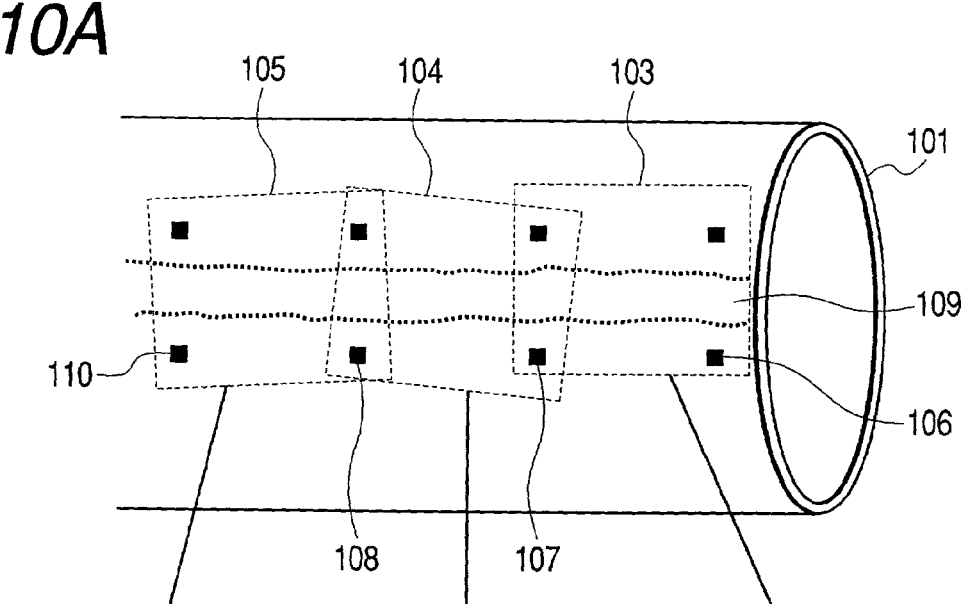
FIG. 10A and FIG. 10B are conception diagrams showing examples of positions and imaging of marks allocated in the equal interval when the welded portions of piping are extended in the longitudinal direction and FIG. 10C is a conception diagram showing the alignment process as a continuous image.
Figure 10B:
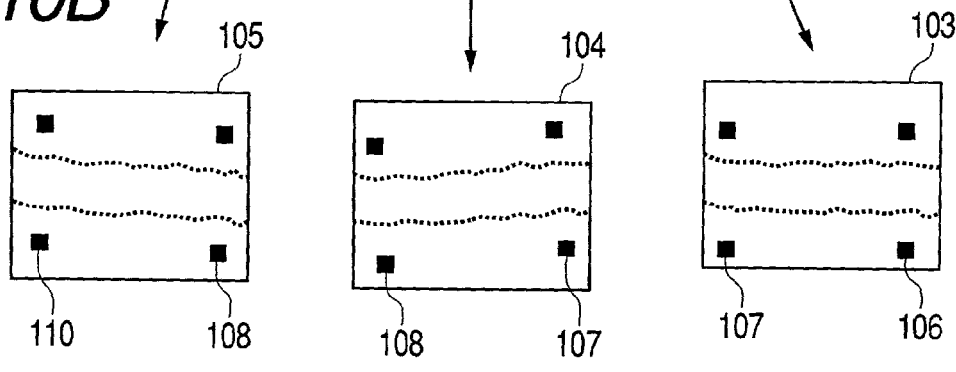
Figure 10C:
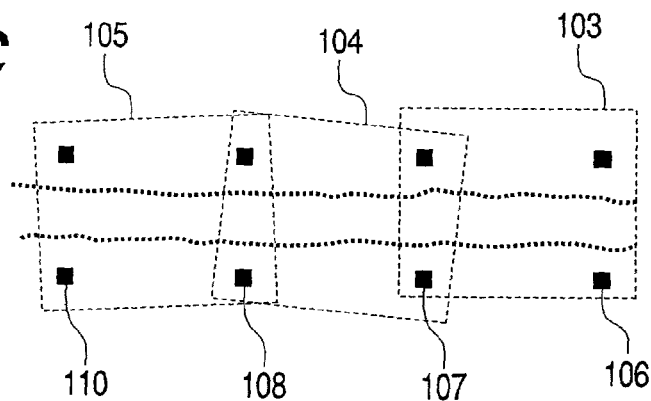
Figure 11A:
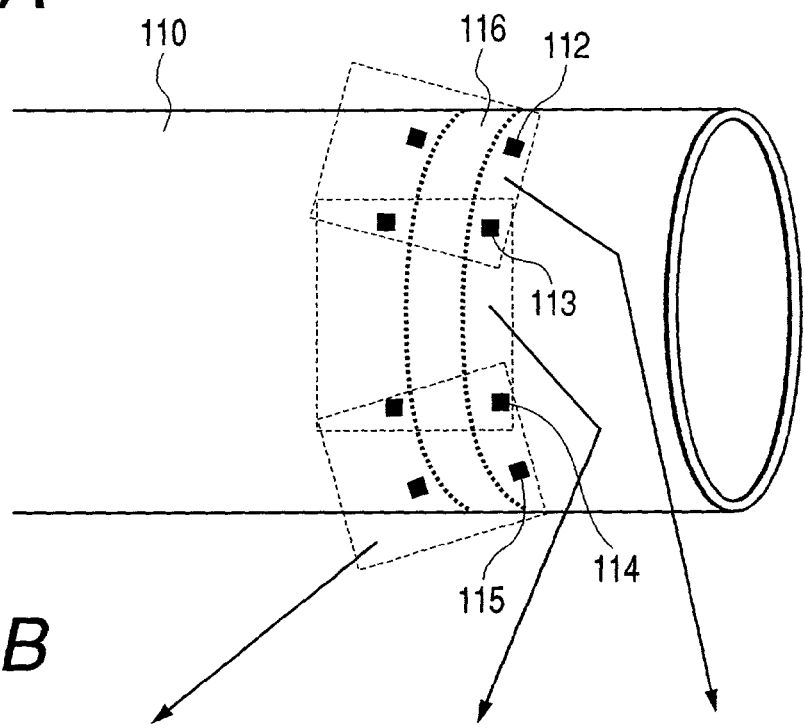
FIG. 11A and FIG. 11B are conception diagrams showing examples of positions and imaging of marks allocated in the equal interval when the welded portions of piping are extended in the circumferential direction and FIG. 11C is a conception diagram showing the alignment process as a continuous image.
Figure 11B:
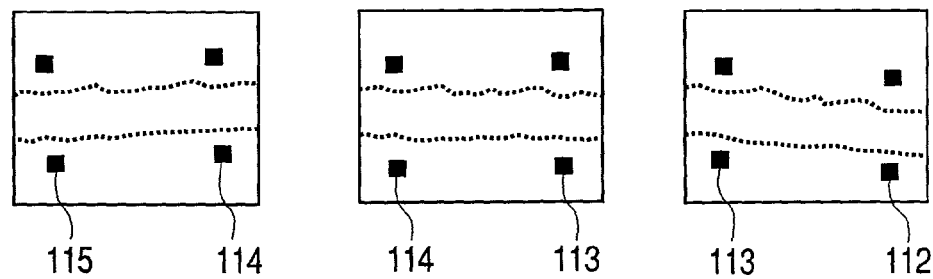
Figure 11C:
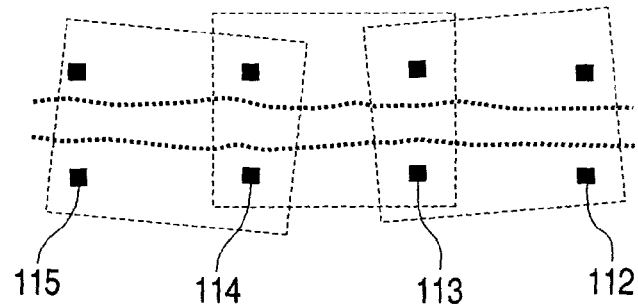

FIGS. 11A to 11C show an example of the liquid penetrant inspection for the welded beads in the circumferential direction of the pipe. Like the processes in FIG. 10, the marks 112 to 115 are allocated in the equal interval, three images are picked up together with the welded beads 116 as shown in FIG. 11B, compensation for magnifying factor, tilt and position is conducted for respective images and these images are aligned to generate a continuous image of FIG. 11C. Since the images in the circumferential direction greatly curved at the inspection plane, the magnifying factor at the center of image is different from that at both end portions. Therefore, the marks 112 to 115 are given in the small interval and the continuous image of FIG. 11C can be generated by aligning the images with reference to the marks.

As shown in FIG. 10 and FIG. 11, the images are aligned and the inspection result of total area of welded surface of a pipe is stored as continuous image information into the computer for the purpose of filing. According to the embodiment shown in FIG. 10 and FIG. 11, there is provided the effect that the images of the part welded continuously are aligned in the higher accuracy and can be checked on the display apparatus as the input image and flaw determining image and moreover the entire part of the welded portion can be evaluated.

Next, an example of the method to set the reference white-color in the color image process will be explained with reference to FIG. 8. The welded beads 82 of a pipe 81 are coated with a developer 83. Thereby, the developer at the inspection surface is dried up to have the white-color and the area generating a flaw changes to the red-color because the penetrant diffuses. The white-color of the developer under the flaw-free condition is defined as the reference color.

The automatic reference setting in the image process can be conducted as explained below. A window 86 around the inspection surface is set to an output image 85 of the digital camera 84 having picked up the image of inspection surface. When distribution of luminance 87 in this window 86 is displayed with the horizontal axis defined to indicate the brightness and the vertical axis defined to indicate the frequency, the distribution obtained shows the peak value 88 at a certain luminance point. This peak value 88 is defined as the luminance value of white-color.

When the window 86 is set for the sufficiently wide area, an overwhelmingly large number of white-color points appear in the peak 88 even when red-color of flaw exists within the window. This value is obtained for three colors of R, G, and B and is subjected to the xy chromaticity conversion. Thereby, the point k in the chromaticity diagram 89 can be obtained. Here, the + point k in the chromaticity diagram 89 has the values of x=0.31 and y=0.32. The red-color of the penetrant diffusing to the flaw point is also plotted on the chromaticity diagram 89. In the subsequent flaw detection processes, a color difference between these two points is used.

Figure 9A:
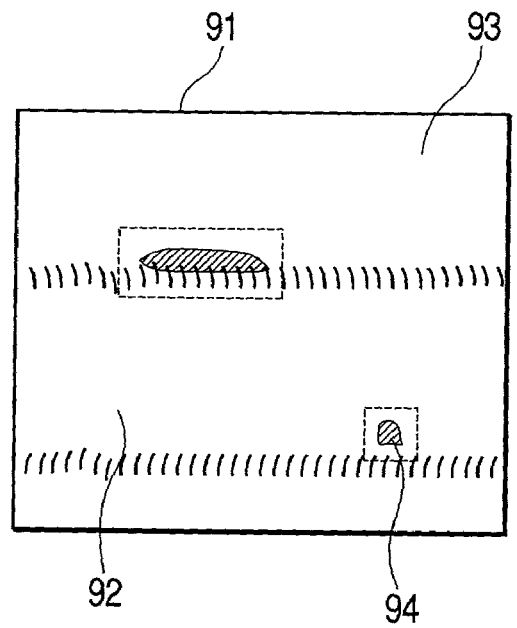
FIGS. 9A and 9B show embodiments of a flaw inspection process of a color image using the image process algorithm of FIG. 8.
Figure 9B:
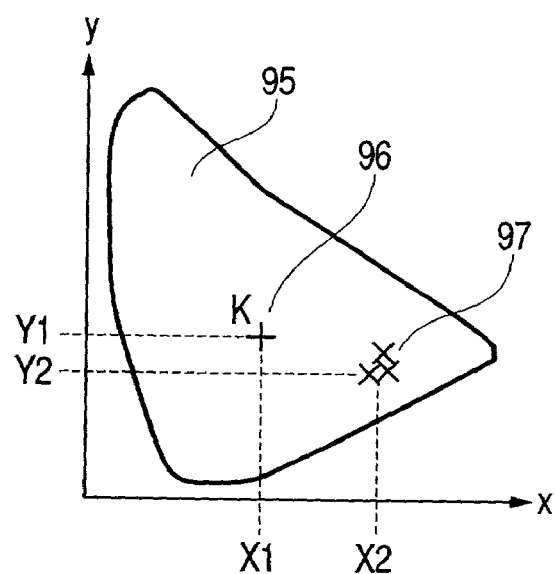

FIG. 9A and FIG. 9B show an example of flaw detection utilizing color images. FIG. 9A shows an image obtained when the liquid penetrant inspection is executed to a pipe having a flaw at the welded portion. In regard to an input image 91, the peripheral area of the welded beads 92 is coated with a penetrant and this condition is left as it is for about 20 minutes. Thereafter, the penetrant is removed by wiping the surface and the welded beads 92 are coated with a developer. As a result, several flaw candidates 94 wherein the penetrant of red-color is diffused out into the white-color 93 of the developer can be visualized.

As a method for detecting a true flaw from these flaw candidates, a factor of color difference is used. The xy chromaticity is calculated from the R, G, B data of every pixels of a color image of FIG. 9A and it is then plotted in the xy chromaticity diagram of FIG. 9B. As shown previously in FIG. 8, the white-color in the developer becomes the point k of white-color 96. A flaw point 94 becomes a sign x 97 of the red-color. Color difference is expressed as (x2−x1) and (y2−y1) and a flaw 94 can be extracted from the image 91 by setting a threshold value between x1 to x2, and between y1 to y2.

A method for extracting a flaw from the color image obtained will be explained in detail with reference to FIG. 12 to FIG. 20.

Figure 12:
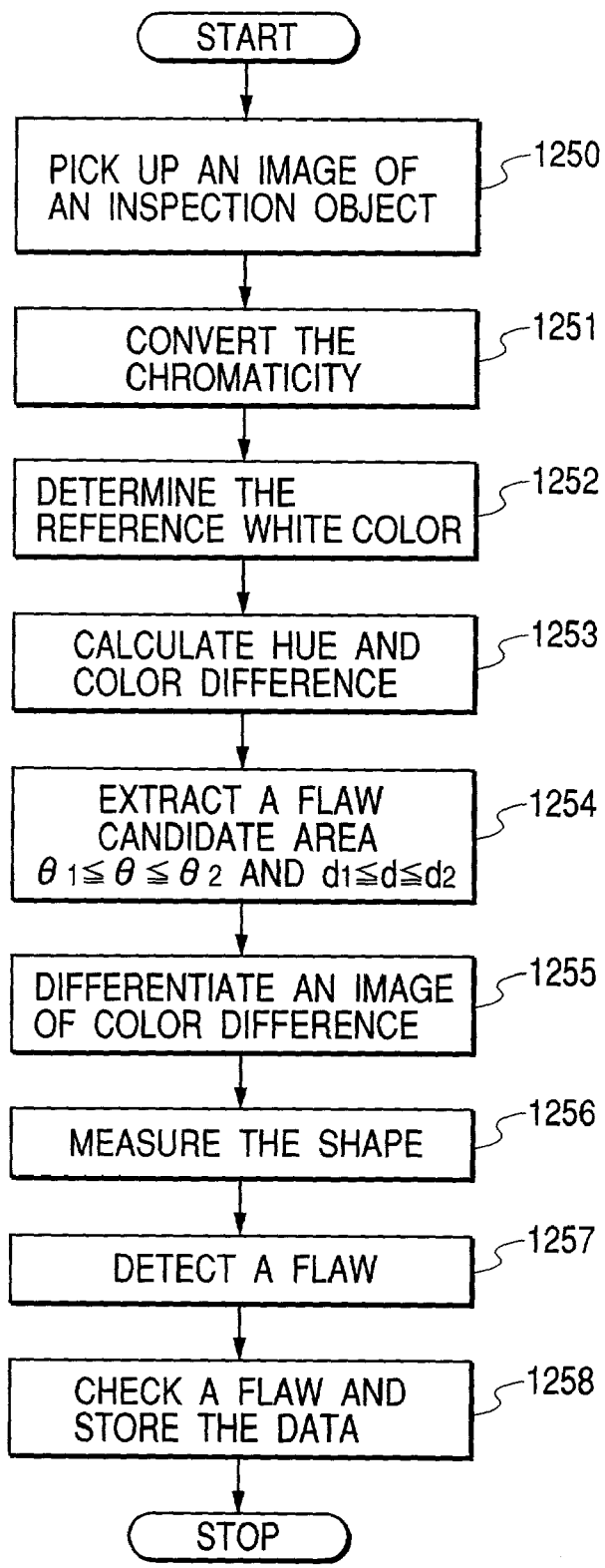
FIG. 12 is a flowchart showing a flow of the automatic inspection method in the liquid penetrant inspection of the present invention.

FIG. 12 shows a flow of processes. First, in the step 1250, an image of the welded part is picked up to obtain a color image and the chromaticity conversion is conducted in the step 1251 in order to obtain the xy chromaticity value of each pixel from the obtained R. G, B color image data. Next, in the step 1252, the reference white-color is determined to calculate the chromaticity of reference white-color of the developer and in the step 1253, the hue and color difference at each position on the image for the reference white-color are calculated. Thereafter, in order to extract a flaw candidate are in the step 1254, an area in the hue and color difference of the particular range is extracted through the binarization process.

From the step 1254, it can be understood that a true flaw has the clear contour part and a pseudo-flaw often has unclear contour part. Therefore, a color-difference image is differentiated in the step 1255 to obtain a changing rate of color difference at the contour of the extracted flaw candidate area. Next, in the step 1256, measurement for shape is executed for area, aspect ratio and length of the flaw candidate area. Thereafter, a flaw is detected in the step 1257 to detect, as the true flaw, only the area having a large changing rate of color difference and length and area larger than the specified ones. Moreover, the inspection result is displayed on the color monitor 24 and thereby an inspection person confirms a flaw. Thereafter, in the step 1258, image data, shape data and position information are filed for storage in the memory device or are printed out for storing as a hard copy.

Figure 13:
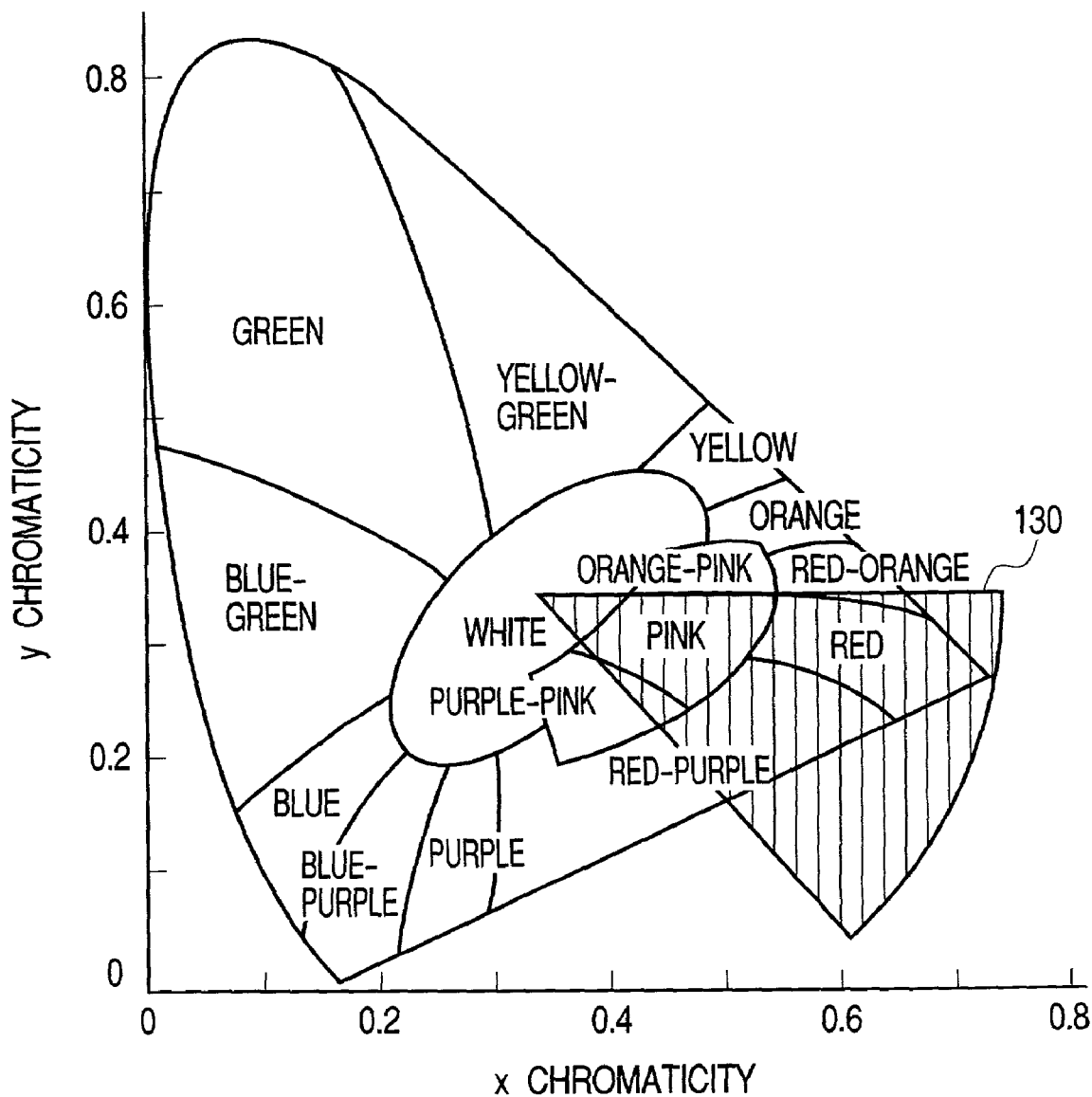
FIG. 13 is an xy chromaticity diagram.

For the inspection based on colors, the color must be evaluated quantitatively. For this purpose, in the step 1251 for the chromaticity conversion, the RGB data of color images picked up are converted to the chromaticity x, y and luminance Y specified with the CIE (Commission Internationale de l'Eclairage) [International Commission on Illumination] and inspection is conducted using these data. The chromaticity of the x, y coordinates expressed on the two-dimensional orthogonal coordinates is called the chromaticity diagram and is shown in FIG. 13. In the chromaticity diagram, the white-color appears at the center and various colors are located around the white-color and various colors become clear as it becomes far from the white-color. Thereafter, tint is called as hue, clearness of each color is called chromaticness, and difference between two chromaticity values on the chromaticity diagram is called color difference. Range of chromaticity 130 in the liquid penetrant flaw inspection is shown in FIG. 13.

Figure 14:
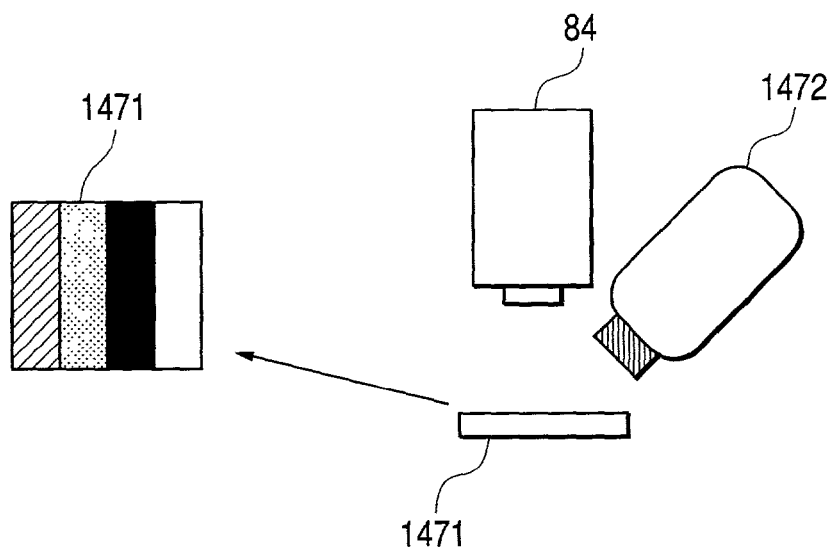
FIG. 14 is a front elevation of the structure of a camera calibration apparatus.
Figure 15:
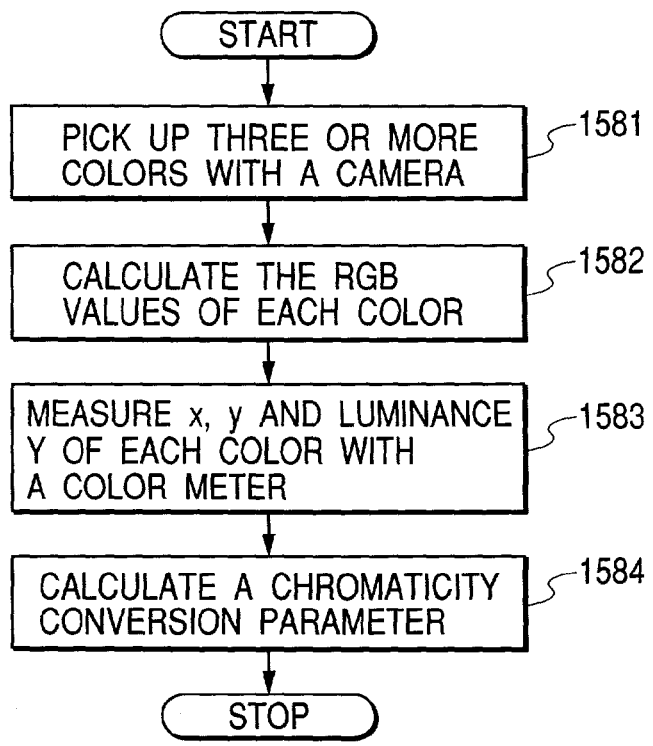
FIG. 15 is a flowchart showing a flow of the camera calibration process.

In this method, in order to realize highly accurate conversion from the RGB data to the chromaticity of x, y and luminance Y, color calibration is conducted previously using a color tag 1471 for camera calibration as shown in FIG. 14. The flow of this process is shown in FIG. 15. The color tag 1471 for camera calibration is painted, for example, with the three or more colors. In the step 1581, an image of the camera calibration color tag 1471 is picked up with the digital camera 84 and the RGB values of each color are calculated in the step 1582. Moreover, in the step 1583, such chromaticity x, y and luminance Y are measured with a color meter 1472. Here, a relationship between the RGB values and xyY value is expressed with the expressions (1), (2).

$$\begin{pmatrix} X \\ Y \\ Z \end{pmatrix} = \begin{pmatrix} a_{11} & a_{12} & a_{13} \\ a_{21} & a_{22} & a_{23} \\ a_{31} & a_{32} & a_{33} \end{pmatrix} \begin{pmatrix} R \\ G \\ B \end{pmatrix} \quad (1)$$

Here, X, Y, Z are called the three-stimulus values.

$$\text{Chromaticity: } x = \frac{X}{X+Y+Z} \quad y = \frac{Y}{X+Y+Z}, \text{ Luminance: } Y \quad (2)$$

Therefore, an intrinsic conversion parameter of camera can be obtained by calculating an xyY value by substituting the RGB values of each color extracting from the camera for the expressions (1), (2) and obtaining $a_{11}$ to $a_{33}$ to provide such value matched with the xyY value measured with a color meter. Since the nine parameters are still unknown, the parameters can be calculated with at least three RGB values $(R_1G_1B_1)$ to $(R_3G_3B_3)$ and the corresponding xyY values of color meter $(x_1y_1Y_1)$ to $(x_3y_3Y_3)$.

Since it is obvious from the expression (2) that the XYZ can be calculated with the following expression (3) from the xyY value, $$X=Yx/y, \ Y=Y, \ Z=Y\times(1-x-y)/y \quad (3)$$

XYZ is obtained by substituting the xyY value of three colors of color meter for the expression (3) and it is then substituted for the expression (1).

$$\begin{pmatrix} X_i \\ Y_i \\ Z_i \end{pmatrix} = \begin{pmatrix} a_{11} & a_{12} & a_{13} \\ a_{21} & a_{22} & a_{23} \\ a_{31} & a_{32} & a_{33} \end{pmatrix} \begin{pmatrix} R_i \\ G_i \\ B_i \end{pmatrix} \ (i=1,2,3) \quad (4)$$

Thereby, the intrinsic conversion parameters $a_{11}$ to $a_{33}$ of camera are obtained in the step 1584 and the xyY value which is equal to the value of color meter can also be obtained from the RGB value of camera.

A profile of the camera calibration color tag 1471 used for the liquid penetrant flaw inspection is just suitable for color calibration in such a case where the reference colors of R, G, B, and W and various colors which change to red-color of the penetrant from the white-color of the developer are allocated.

The white-color similar to that of developer which changes to red-color, pink-color of a flaw candidate and red-color corresponding to that of a flaw are selected step by step from the range of chromaticity 130 for the liquid penetrant flaw inspection image of FIG. 13, the xyY value is measured with a color meter 1472 and this xyY value is compared with each xyY value calculated from the conversion parameter of the intrinsic xyY value of the camera to be used. Thereby, reproducibility of the conversion parameter can be confirmed. Accordingly, highly reliable and accurate chromaticity measurement can be realized easily by confirming reproducibility of color using periodically (preferably, before the flaw inspection work) the color tag 1471 of FIG. 14 during the liquid penetrant flaw inspection work.

Moreover, since the reference color of color tag is different depending on color temperature of the light source for the lighting, it is necessary to select the chromaticity for calibration depending on the light source. In addition, chromaticity of colors from white-color to red-color is different due to the difference of tint (surface of metal such as stainless and dark surface of black skin of iron or the like or brown surface of rust or the like) depending on the surface condition of the inspection object. Therefore, the number of interpolation colors of white-color, pink-color and red-color is increased and thereby conversion to the xyY value can be conducted in the higher accuracy as the color calibration is continued.

Moreover, it is also preferable to select the reference colors of red, green, blue and white also select chromaticity changing to the red-color from the white-color depending on the chromaticity of the developer and penetrant.

Figure 16A:
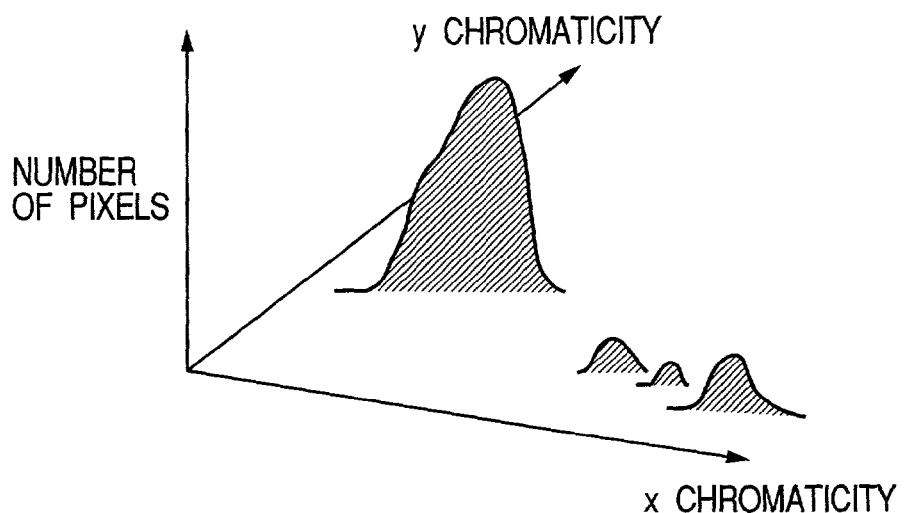
FIGS. 16A, 16B and 16C are diagrams showing a method for obtaining the chromaticity of reference white from a color difference image.
Figure 16B:
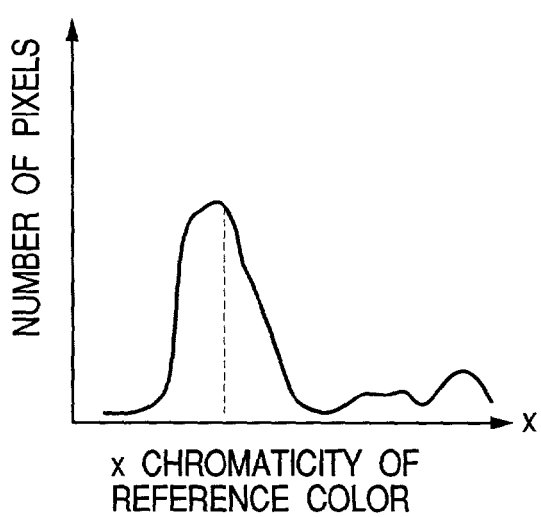
Figure 16C:
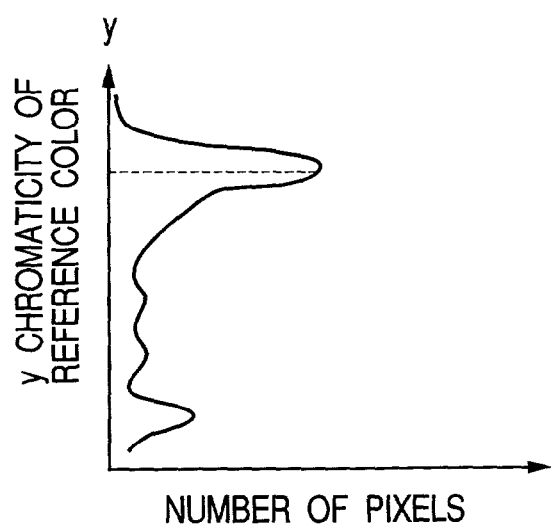

Using the intrinsic parameters of camera previously calculated by calibration, the RGB value obtained from the camera is converted in the chromaticity to the xyY value and distribution of chromaticity in the image is calculated. Thereafter, the chromaticity value of developer is calculated from the image, namely the chromaticity of the normal area is calculated as the reference value in the step 1252 of FIG. 12. First, the chromaticity x, y of each pixel in the image is searched, and the number of pixels having each x, y value as shown in the graph of FIG. 16A is counted in order to generate a two-dimensional chromaticity distribution. Thereafter, the x chromaticity value of the image including the largest number of pixels shown in FIG. 16B and they chromaticity shown in FIG. 16C are obtained. Since the greater part of the image does not have any flaw, the x, y chromaticity value of the peak value in the two-dimensional chromaticity distribution becomes equal to the xy chromaticity value of the reference white color.

Next, the hue and color difference at each position on the image for this reference white-color are calculated in the step 1253 of FIG. 12.

Figure 17A:
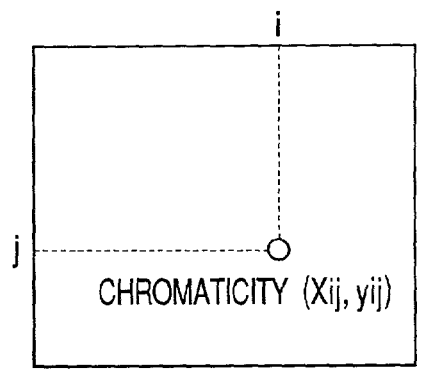
FIGS. 17A, 17B and 17C are diagrams for explaining a method for calculating hue on the chromaticity diagram.
Figure 17B:
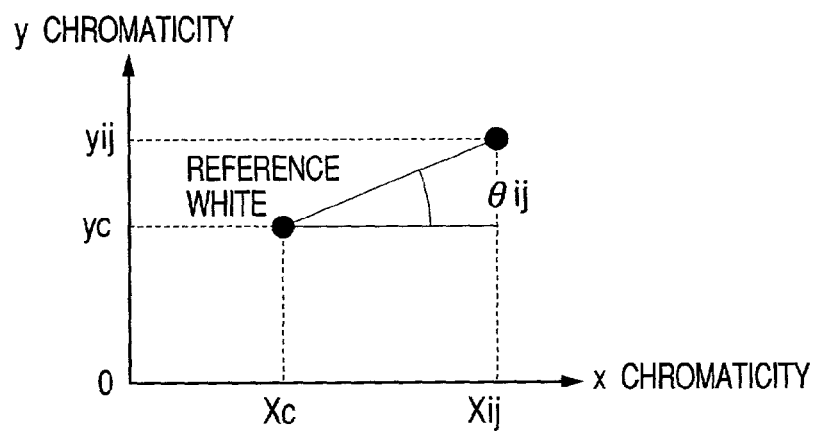
Figure 17C:
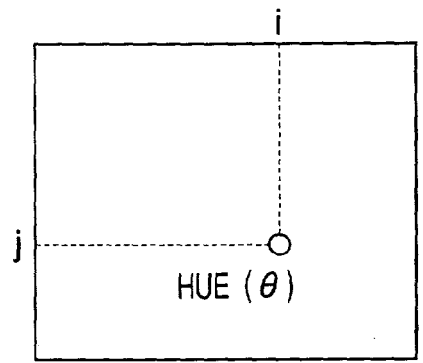

When the chromaticity of reference white-color is defined as ($x_c$, $y_c$) and chromaticity at the position (i, j) on the image as ($x_{ij}$, $y_{ij}$) the hue at the position (i, j) is calculated in the direction toward the reference color on the chromaticity diagram as shown in FIG. 17A to FIG. 17C.

The calculation expression is indicated as (5).

$$\text{Hue}: \theta_{ij} = \tan^{-1}\left(\frac{y_{ij} - y_c}{x_{ij} - x_c}\right) \quad (5)$$

Figure 18A:
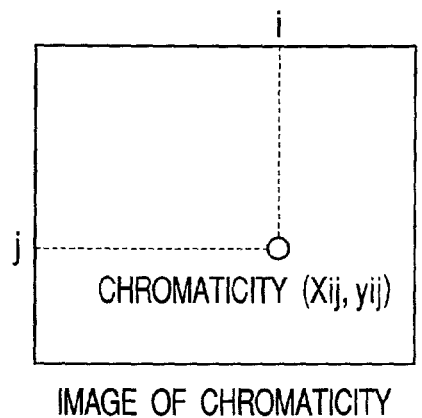
FIGS. 18A, 18B and 18C are diagrams for explaining a method for calculating color difference on the chromaticity diagram.
Figure 18B:
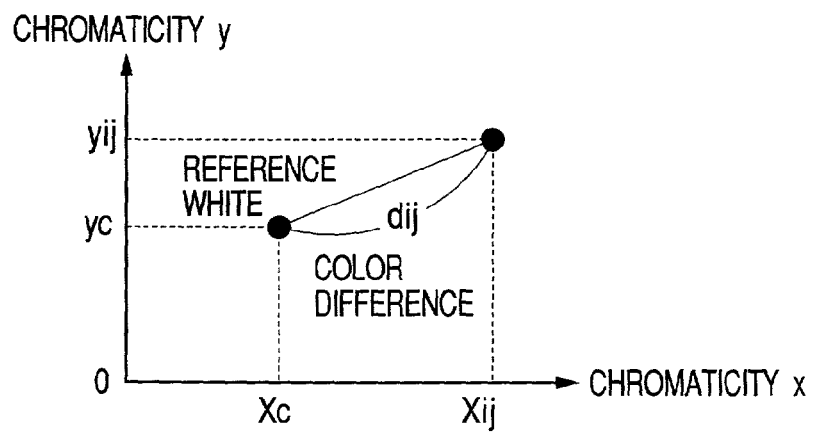
Figure 18C:
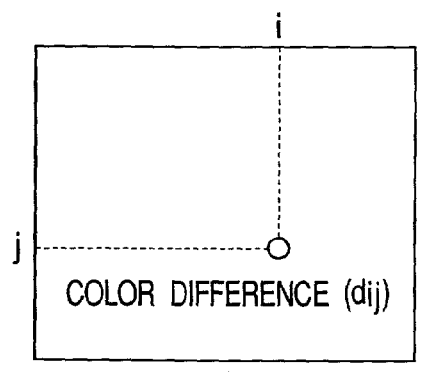

Moreover, color difference at the position (i, j) is calculated in terms of the distance from the reference color on the chromaticity diagram as shown in FIG. 18A to FIG. 18C. The calculation expression is indicated as (6).

$$\text{Color Difference}: d_{ij} = \sqrt{(x_{ij} - x_c)^2 + (y_{ij} - y_c)^2} \quad (6)$$

Figure 19:
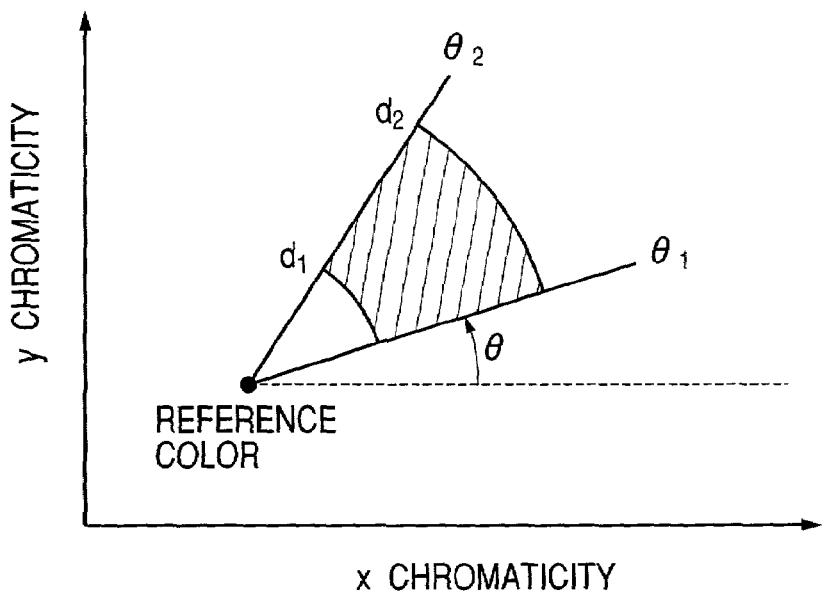
FIG. 19 is a graph of the x chromaticity and y chromaticity showing a method for obtaining a flaw candidate area from the hue obtained in FIG. 17 and color difference obtained in FIG. 18.

A range to be detected as a flaw area depending on the hue (in the figure, the range where the hue θ is set to $\theta_1 \leq \theta \leq \theta_2$) is restricted as shown in FIG. 19 from the hue and color difference at each position of the image for the reference white-color calculated as explained above and a degree of difference of clearness of color from the reference white-color is restricted with color difference (in the figure, the range where the color difference d is set to $d_1 \leq d \leq d_2$). Moreover, an area within this range is extracted as the flaw candidate area.

Here, the flaw candidates obtained by restricting the range with the hue and color difference as explained above also include the areas which are not required to be detected as the flaw. For example, an area in which the chromaticity changes gradually for the reference white-color never generates a flaw and an area detected as a flaw always has the clear contour.

Therefore, an area showing gradual change of color for the color of peripheral area is assumed as a pseudo-flaw and only the area showing sudden change of color is assumed as a flaw.

In the step 1255 of FIG. 12, a change of color difference from the reference white-color in the flaw candidate area is obtained and only the area having such change larger than a constant value is assumed as a flaw.

Figure 20A:
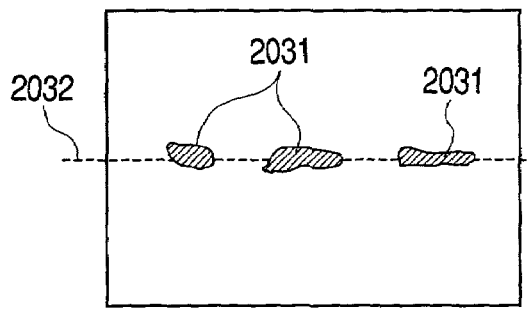
FIGS. 20A, 20B, 20C and 20D are diagrams showing a method for obtaining a flaw area by determining an artificial flaw from the flaw candidate area obtained in FIG. 19.
Figure 20C:
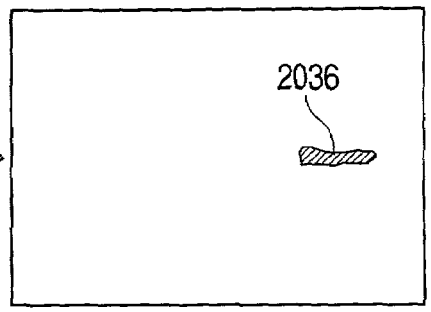
Figure 20B:
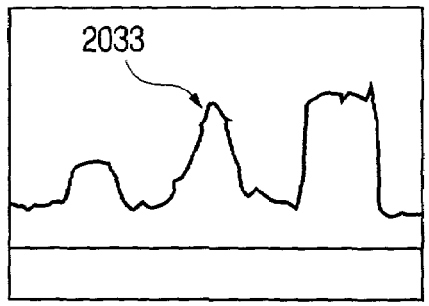
Figure 20D:
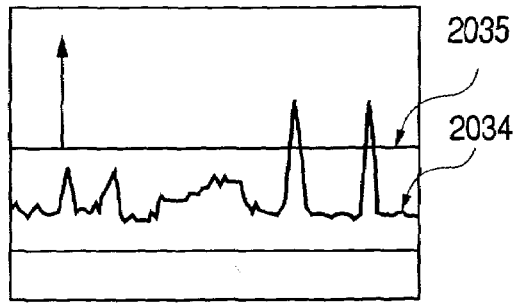

With reference to FIGS. 20A, 20B, 20C, and 20D, a flaw candidate area 2031 extracted in the step 1254 of FIG. 12 is indicated in FIG. 20A. Numeral 2033 of FIG. 20B indicates a graph of color difference for the reference white-color on the line 2032 shown in FIG. 20A. Moreover, differential distribution of color difference 2034 shown in FIG. 20D can be obtained from the change of color difference 2033 at each position on the line 2032, namely by differential operation of the color difference 2033. When change of color difference for the reference white-color is small, a differential value also becomes small as explained above. Here, as shown in FIG. 20D, only the area where the differential value is larger than a constant value 2035 is defined as a flaw area. As a result, only the area providing a large color difference and a large change of color difference as shown in FIG. 20C, namely only an area having clear contour is detected as the flaw area 2036.

Next, a method for determining a threshold value 2035 will be explained with reference to FIG. 21.

Figure 21A:
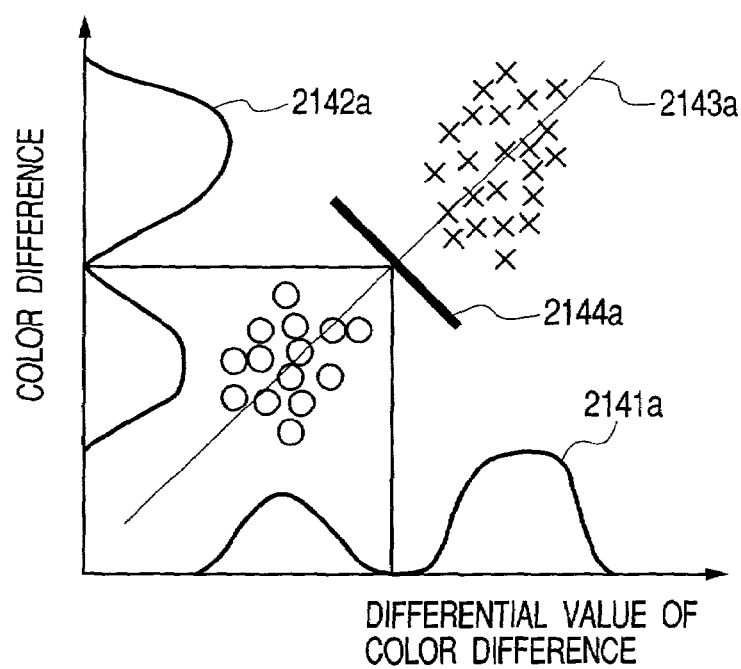
FIGS. 21A and 21B are diagrams for explaining a method for obtaining a threshold value to obtain a flaw area by determining an artificial flaw from the flaw candidate area shown in FIG. 20.
Figure 21B:
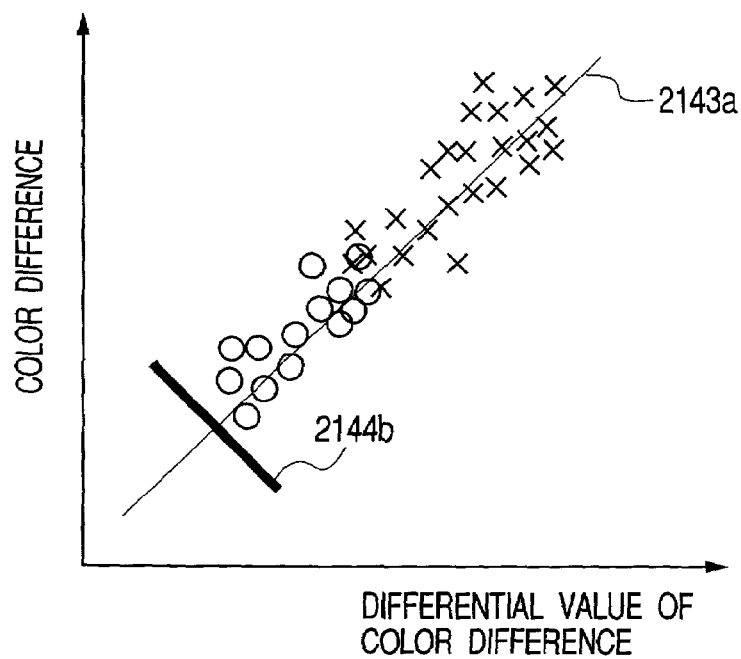

In the graph of FIG. 21A, with the maximum value of color difference in each flaw candidate area extracted with hue and color difference assigned on the vertical axis and the maximum value of color difference differential value of the contour of each flaw area assigned on the horizontal axis, the values of true flaws are plotted with x, while values of pseudo flaws are plotted with o. Moreover, 2141a indicates frequency distribution of each color difference differential value, while 2142a indicates frequency distribution of color difference value. When a flaw and a pseudo flaw are clearly separated, the Good/No-good determination line 2144a becomes, as shown in FIG. 21A, a linear line 2144a which passes an intersecting point passing the peak value of the valley of the frequency distribution of the 2141a and 2142a and is vertical to the inertia main axis 2143a of the plotted points. Moreover, a flaw and a pseudo flaw are not separated, namely when there is no peak of the valley of the frequency distribution, the determination line is defined as 2144b as shown in FIG. 21B and thereby all flaw candidate areas can be detected as the flaw without any erroneous detection and overlooking.

Figure 22:
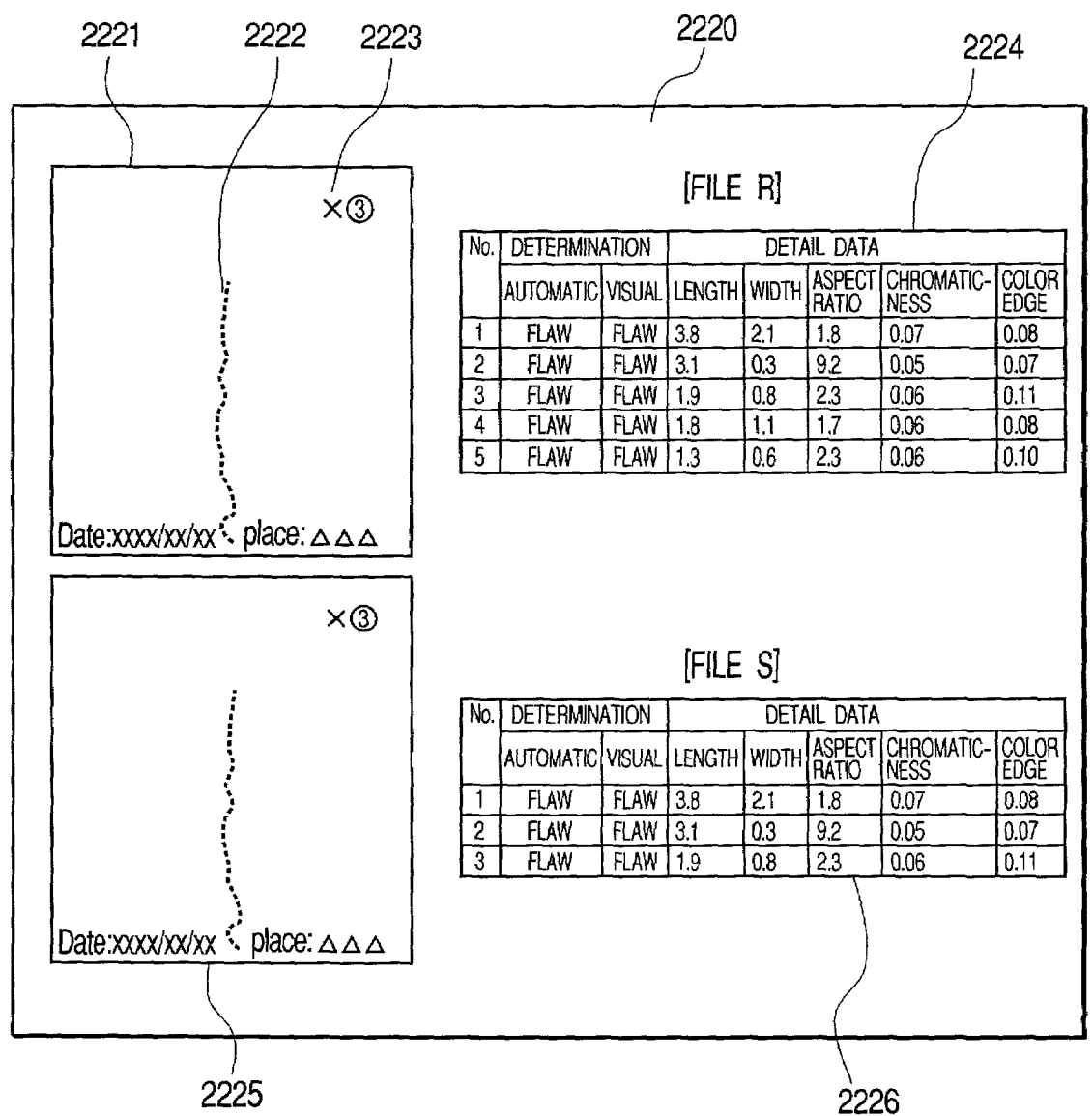
FIG. 22 shows an example of a data filing system, namely an image file format in which characteristics of data of the detected flaw are defined as the similarity.

Next, an example of the profile of image filing is shown in FIG. 22. An input image 2221 includes a flaw 2222 and a mark 2223 is simultaneously displayed in the same image. As the amount of characteristics, the detail data 2224 of the detected flaw includes length, width, aspect ratio, chromaticness and color edge (differential value of chromaticness). These values are recorded as the file R to a computer in association with the image 2221. The numerical items in the file can be picked up as the similar image of the other image. For example, the image 2225 of file S and detail data 2226 have been re-inspected after six months of the filing of file R. Here, these are displayed on the basis of the similarity item of inspection position.

FIGS. 23A, 23B, 23C, 23D, 23E and 23F show examples of filings for similarity of information pieces such as material, Yes or No of inspection for welding, name of field, name of factory, name of plant, name of building, name of piping system, piping number, diameter of piping, thickness of pipe and time of implementation or the like. FIG. 23A shows the inspection fields A to P plotted on a map. FIG. 23B shows areas of the facility. This figure shows that the facilities B1, B2, and B3 are provided in the inspection field, for example, in the factory A. Moreover, FIG. 23C shows a piping system. This figure shows a simplified model and the actual facility is considerably complicated. The piping of FIG. 23C is welded at the areas C1, C2 and C3. A result of liquid penetrant flaw inspection for the welded area C2 is shown in FIG. 23D. The inspection result in the embodiment shows that flaws are recognized at a couple of areas of area 1 and area 2. FIG. 23E shows an example wherein such image data are filed for respective items in FIGS. 23A to 23D. FIG. 23F shows an example of monitor displays of the P image, for example, of the inspection date in Sepember, 1999('99/9) and of the Q image of the inspection date in March, 2000 ('00/3) obtained from such file.

In this embodiment, a profile of image file using the similarity P and similarity Q and search content are searched and displayed from the plant in a certain filed as explained above, but since comparison in shapes of flaws and progressing condition of flaw inspection can be checked quickly from the search and display for the similar inspection result even for the plant facilities in various countries in the world including, of course, a certain area in Japan, this embodiment provides excellent effect in reliability of flaw inspection.

Figure 24:
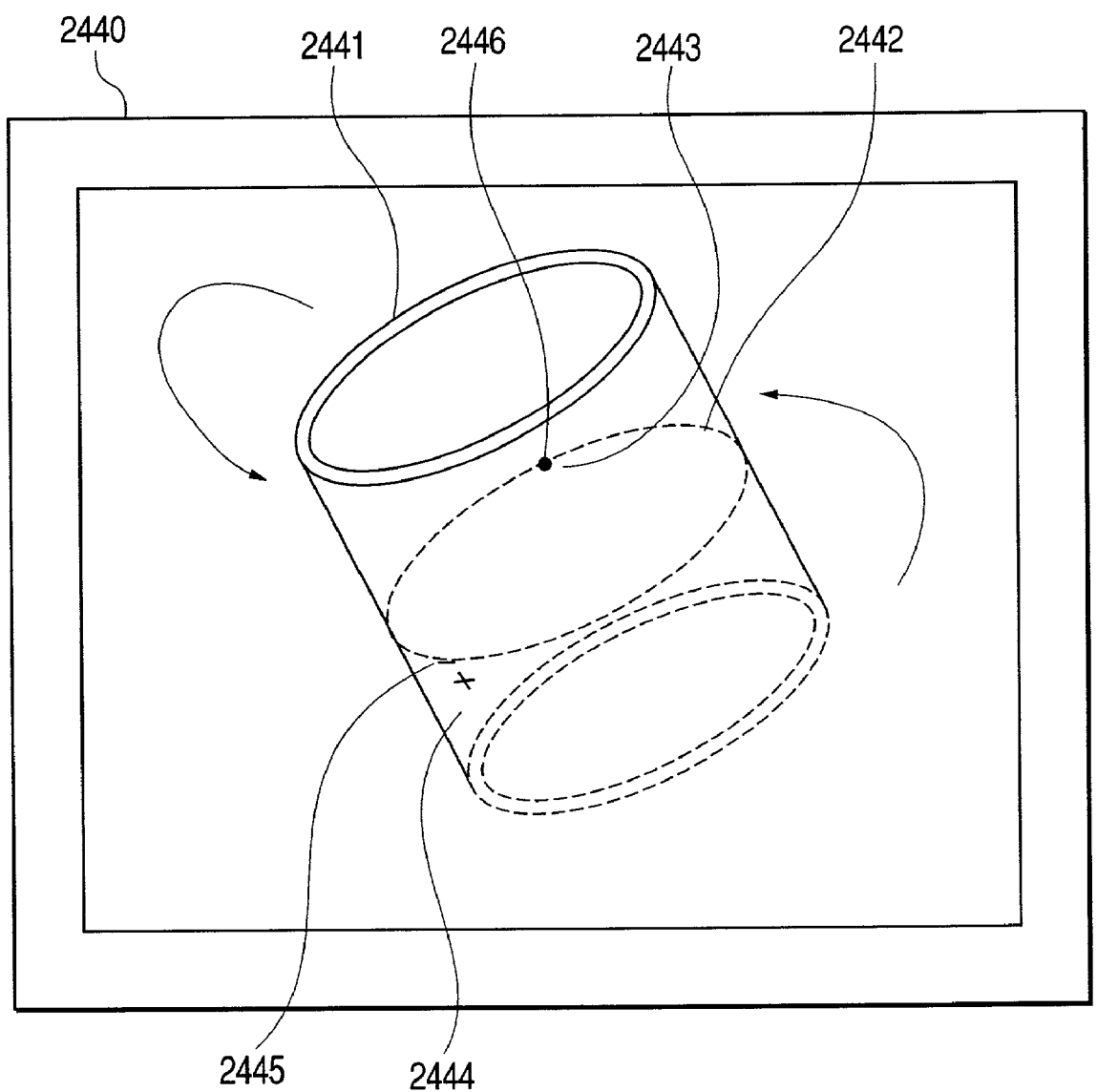
FIG. 24 is a diagram showing an example of three-dimensional display on the monitor of the result of liquid penetrant inspection.

Next, an example of a means for displaying in three-dimension an image by aligning continuous image information pieces is shown in FIG. 24.

FIG. 24 is an embodiment wherein an entire image re-structured in the shape of three-dimensions is displayed on the display 2440 based on the detail sizes of piping 2441. In this figure, flaws 2443, 2445 of the welded beads 2442 and marks 2444, 2446 are also displayed simultaneously. Condition of flaw can clearly be detected by displaying this image through variations of rotating and tilting angles by manipulating a keyboard and a mouse of the computer. As explained above, easier detection of the conditions of flaw results in the effect that an area to generate a stress and a crack in the actual usage condition can be determined easily and therefore the data obtained can be fed back for selection of material and design of structure.

Although explained in regard to the liquid penetrant flaw inspection, in the case where an inspection object is formed of a magnetic material in this embodiment, the present invention can also be applied to the magnetic particle flaw inspection wherein the inspection object is magnetized with coating of the liquid including fluorescent magnetic particle and emission of fluorescent material from a flaw area in which the magnetic flux is concentrated is detected for inspection by irradiating the inspection object with the ultraviolet ray. In this case, in regard to the structure of digital camera system 200 shown in FIG. 2, a light source to generate the ultraviolet ray is used in place of the LED ring light 202 and it is enough for the digital camera 201 to introduce a structure suitable for detection with higher efficiency of the fluorescent material generated from a flaw area without any influence of disturbance light, for example, a structure that is provided with a filter for detection of fluorescent material.

According to the present invention, it is possible to solve the problems of prior art and provide the following effects.

(1) In the case of visual inspection, since an image can be inputted with an image pickup apparatus such as a digital camera or the like, although the inspection result is different from personal difference of an inspection person, quantitative and stable evaluation for flaw area can be realized.

(2) A highly reliable data can be stored by adding an input image and flaw detection process result in the computer to a report of inspection result.

(3) Connection of a video signal cable and a power supply cable to the computer is no longer required by combining a battery-driven lighting apparatus such as the LED ring lighting device to a cordless type image pickup apparatus such as a digital camera and thereby portability of apparatus can be improved to realize the liquid penetrant flaw inspection in every areas under any environmental condition.

(4) When an image is inputted with an image pickup apparatus such as a digital camera or the like, difference in the image magnifying factor and tilt which are easily generated can be compensated on the off-line basis by allocating marks and lines given in the equal interval within the image.

(5) Moreover, in the inspection of a long-length piping system, the inspection result can be searched using a keyword of the characteristics of a file by aligning several images to a continuous image of piping and then filing such image including the information of inspection object and inspection data thereof.

(6) Moreover, since the liquid penetrant flaw inspection method of the present invention does not give any limitation on the operational environment of the image pickup apparatus, it can be effectively used for inspection of bridge, axles of vehicle to which a load is applied, or inspection of pressure device and micro-crack in addition to the piping facilities.

The invention may be embodied in other specific forms without departing from the spirit or essential characteristics thereof. The present embodiment is therefore to be considered in all respects as illustrative and not restrictive, the scope of the invention being indicated by the appended rather than by the foregoing description and all changes which come within the meaning and range of equivalency of the claims are therefore intended to be embraced therein.

What is claimed is:

1. A method for non-destructive inspection of a flaw area in an inspection object, comprising the steps of:

dividing the inspection area of said inspection object into a plurality of areas each of which is provided with a plurality of positioning marks, imaging said divided areas and obtaining a plurality of digital images of said inspection object, said digital images each including the plurality of positioning marks and at least one of said plurality of positioning marks in each of said digital images being shared with one other of said digital images;

storing a plurality of said digital images into a storing means;

compensating for a tilt between the digital images among the plurality of digital images stored in said storing means by displaying one of said plurality of digital images on a screen on which a plurality of reference marks, each of which corresponds to one of said positioning marks, are displayed, and matching each of said positioning marks of said displayed digital image to each of said plurality of reference marks displayed on said screen; and detecting a flaw using each digital image of said compensated digital images.

2. A method according to claim 1, wherein the step of compensating for a tilt among digital images is provided to compensate for a magnifying factor together with a tilt between digital images among a plurality of digital images stored in said storing means.

3. A method according to claim 1, wherein a step of displaying an image of a detected flaw on a display, image together with information of characteristics of an image of said flaw is also provided.

4. A method according to claim 1, wherein each digital image of a plurality of digital images of said inspection object includes a partial image of adjacent divided areas among the inspection areas of said inspection object divided into a plurality of inspection areas.

5. A method for non-destructive inspection of a flaw area in an inspection object, comprising the steps of:

storing a plurality of digital images of a plurality of contiguous areas of an inspecting object into a storing means, said digital images each having a plurality of positioning marks and at least one of said positioning marks in each of said digital images being shared with one of the other of said digital images;

transmitting the plurality of digital images stored in said storing means via a communicating means;

receiving the plurality of said transmitted digital images;

compensating for tilt between digital images based on said received digital images and based on position information of said position marks including displaying one of said plurality of digital images on a screen on which a purality of reference marks, each of which corresponds to one of said positioning marks, are displayed, and matching each of said positioning marks of said displayed digital image to each of said plurality of reference marks displayed on said screen; and detecting a flaw using said each digital image.

6. An apparatus for non-destructive inspection of a flaw area in an inspection object, comprising:
- an image acquiring means for acquiring digital images of said inspection object by picking up images of inspection areas of said inspection object, each of said digital images including a plurality of positioning marks provided in each of said inspection areas and at least one of said positioning marks in each of said digital images is shared with one other of said digital images;
- a storing means for storing a plurality of digital images for the entire part of said inspection areas obtained by sequentially picking up said inspection areas in the viewing field which is smaller than said inspection areas of said image acquiring means;
- a display means for displaying one of said acquired digital images and a plurality of reference marks, each of said plurality of reference marks corresponding to one of said positioning marks in each of said digital images;
- a tilt compensating means for obtaining and compensating for a tilt between digital images among a plurality of digital images for the entire part of said inspection areas stored in said storing means by displaying one of said plurality of digital images on a screen on which said plurality of reference marks are displayed and matching each of said positioning marks of said displayed digital image to each of said plurality of reference marks displayed on said screen; and
- a flaw candidate extracting means for extracting flaw candidates by processing each digital image of which tilt is compensated with said tilt compensating means.

7. An apparatus for non-destructive inspection according to claim 6, wherein a magnifying factor compensating means for—compensating for a magnifying factor of each image among a plurality of digital images stored in said storing means is further provided.

8. An apparatus for non-destructive inspection according to claim 6, wherein said display means displays an image of flaw selected from—said flaw candidate images on the display image together with the information pieces of characteristics of image of said flaw area.

* * * * *